(12) United States Patent
Hornyak et al.

(10) Patent No.: US 10,920,194 B2
(45) Date of Patent: Feb. 16, 2021

(54) FUNCTIONAL MYELINATION OF NEURONS

(71) Applicants: The University of Maryland, Baltimore, Baltimore, MD (US); The United States of America as represented by the Department of Veterans Affairs, Washington, DC (US)

(72) Inventors: Thomas Hornyak, Bethesda, MD (US); Sandeep Joshi, Elkridge, MD (US)

(73) Assignees: UNIVERSITY OF MARYLAND, BALTIMORE, Baltimore, MD (US); THE UNITED STATES OF AMERICA AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 137 days.

(21) Appl. No.: 15/802,845

(22) Filed: Nov. 3, 2017

(65) Prior Publication Data
US 2018/0057790 A1 Mar. 1, 2018

Related U.S. Application Data

(63) Continuation of application No. 14/838,345, filed on Aug. 27, 2015, now abandoned.

(60) Provisional application No. 62/042,975, filed on Aug. 28, 2014.

(51) Int. Cl.
| | |
|---|---|
| *C12N 5/0797* | (2010.01) |
| *A61K 35/36* | (2015.01) |
| *C12N 5/079* | (2010.01) |
| *C12N 5/071* | (2010.01) |

(52) U.S. Cl.
CPC ............ *C12N 5/0623* (2013.01); *A61K 35/36* (2013.01); *C12N 5/0622* (2013.01); *C12N 5/0626* (2013.01); *C12N 2501/115* (2013.01); *C12N 2501/125* (2013.01); *C12N 2501/33* (2013.01); *C12N 2501/365* (2013.01); *C12N 2501/86* (2013.01); *C12N 2502/081* (2013.01); *C12N 2506/091* (2013.01)

(58) Field of Classification Search
None
See application file for complete search history.

(56) References Cited

U.S. PATENT DOCUMENTS

| | | | | |
|---|---|---|---|---|
| 6,033,660 A | * | 3/2000 | Mather ................ | C12N 5/0622 424/93.7 |
| 2002/0146395 A1 | * | 10/2002 | Weinstein .......... | C07K 14/4705 424/93.21 |
| 2007/0264277 A1 | * | 11/2007 | Behrens ................ | C07K 14/53 424/185.1 |

FOREIGN PATENT DOCUMENTS

WO 2017085691 5/2017

OTHER PUBLICATIONS

Amoh et al. "Multipotent hair follicle stem cells promote repair of spinal cord injury and recovery of walking function", Cell Cycle 7(12): 1865-1869, 2008 (Year: 2008).*
Joshi et al. "CD34 defines melanocyte stem cell subpopulations with distinct regenerative properties." PLoS genetics 15.4 (2019): e1008034. (Year: 2019).*
Bixby, S., et al., "Cell-intrinsic differences between stem cells from different regions of the peripheral nervous system regulate the generation of neural diversity," Neuron, 2002, pp. 643-656, vol. 35, No. 4.
Blanpain et al., "Self-renewal, multipotency, and the existence, and the existence of two cell populations within an epithelial stem cell niche," Cell 118, 2004, vol. 115, No. 5, pp. 635-648.
Braun, K., et al., "Manipulation of stem cell proliferation and lineage commitment: visualization of label-retaining cells in whole mounts of mouse epidermis," Development, 2003, pp. 5241-5255, vol. 130, No. 21.
Estrach, S., et al., "Jagged 1 is a beta-catenin target gene required for ectopic hair follicle formation in adult epidermis," Development, 2006, pp. 4427-4438, vol. 133, No. 22.
Hoffman, "The potential of nestin-expressing hair follicle stem cells in regenerative medicine," Expert Opinion on Biological Therapy, 2007, vol. 7, No. 3, pp. 289-291.
Pfaltzgraff, E., et al., "Isolation and culture of neural crest cells from embryonic murine neural tube," J Vis Exp., 2012, p. e4134, No. 64.
O'Meara, R., et al., "Derivation of enriched oligodendrocyte cultures and oligodendrocyte/neuron myelinating co-cultures from post-natal murine tissues," J Vis Exp., 2011, Epublication, vol. 21, No. 54, doi: 10.3791/3324.

(Continued)

*Primary Examiner* — Emily A Cordas
(74) *Attorney, Agent, or Firm* — Wolter Van Dyke Davis, PLLC; Martha Cassidy

(57) ABSTRACT

Hair follicle bulge region/LLP region CD34(+) MeSCs can be isolated from mammalian skin bearing hair follicles. These cells are multipotent and retain the ability to differentiate into cells of neural crest lineage, including glia-like cells that express the glial marker Gfap, and are able to express myelin basic protein, and to remyelinate naked (unmyelinated or demyelinated) neuronal processes with a functional, dense myelin sheath. These cells of neural crest lineage can be used to produce a dense myelin sheath on neurons which lack myelin due to genetic defect, trauma, toxin, infection, or disease process. Therefore, embodiments of the invention provide methods for preparing such cells, the cells themselves and compositions containing the cells, as well as methods for using the cells.

7 Claims, 16 Drawing Sheets
Specification includes a Sequence Listing.

(56) References Cited

OTHER PUBLICATIONS

Okamoto et al., "A melanocyte-melanoma precursor niche in sweat glands of volar skin," Pigment Cell & Melanoma Research, 2014, vol. 27, No. 6, pp. 1039-1050.
Zeltner, et al., "Feeder-free Derivation of Neural Crest Progenitor Cells from Human Pluripotent Stem Cells," Journal of Visualized Experiments, 2014, vol. 87, pp. 1-9.
Young, R.D. and Oliver, R. F. "Morphological changes associated with the growth cycle of vibrissal follicles in the rat," J. Embryol, exp. Morph, 1976, vol. 36, pp. 597-607.

* cited by examiner

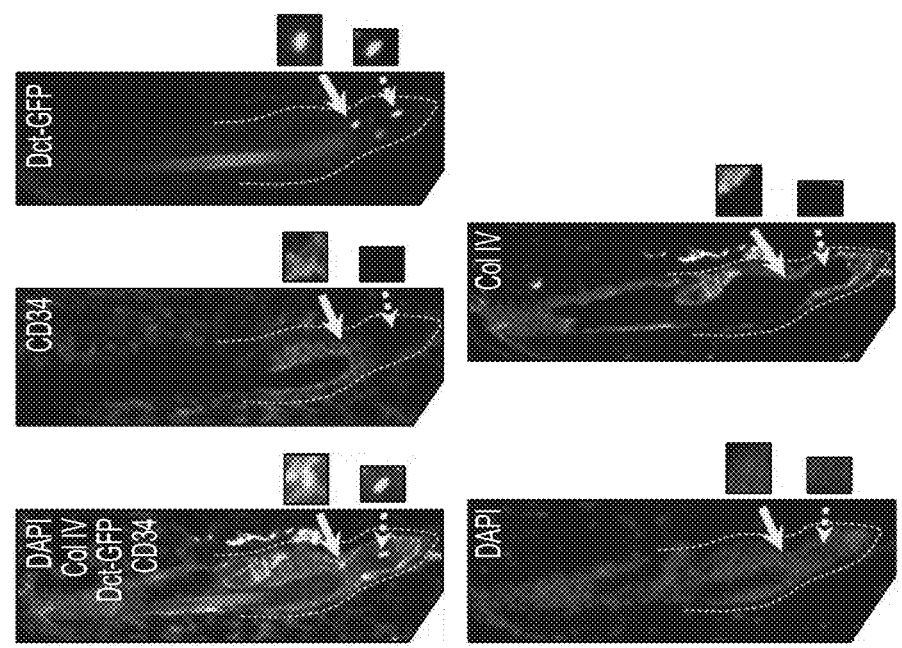
FIG. 1E
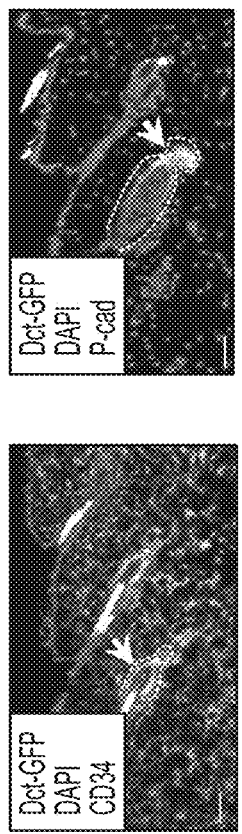
FIG. 1A
FIG. 1B
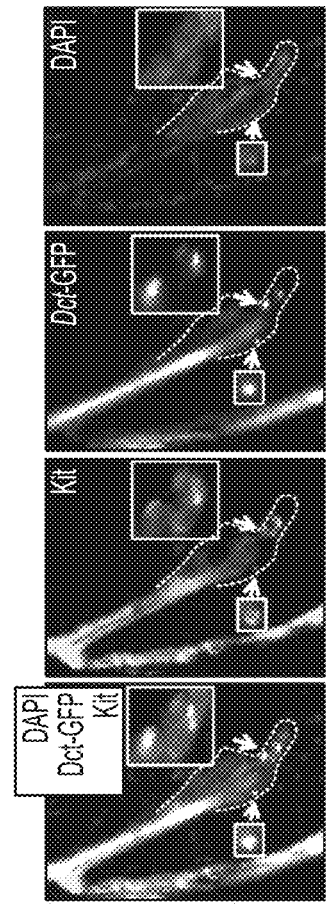
FIG. 1C
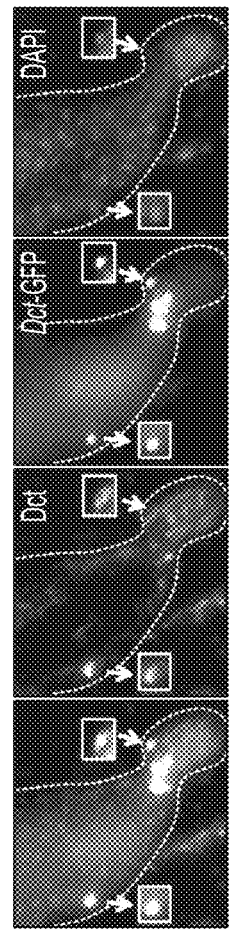
FIG. 1D

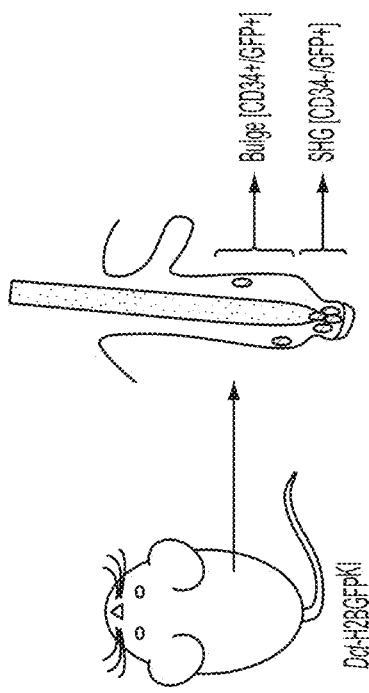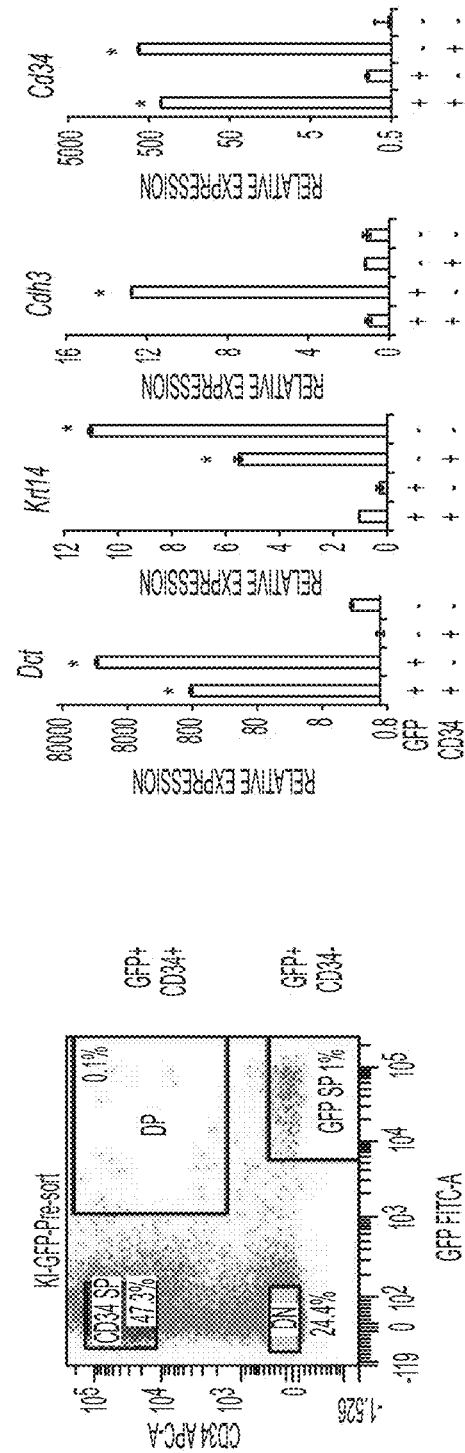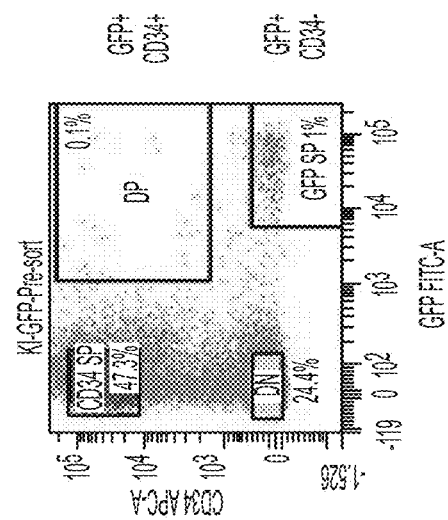

 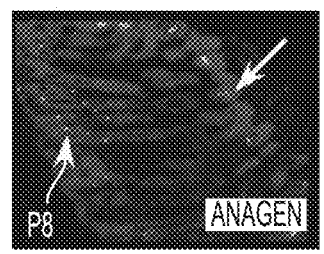 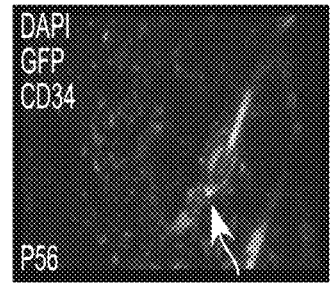
FIG. 6A  FIG. 6B  FIG. 6C
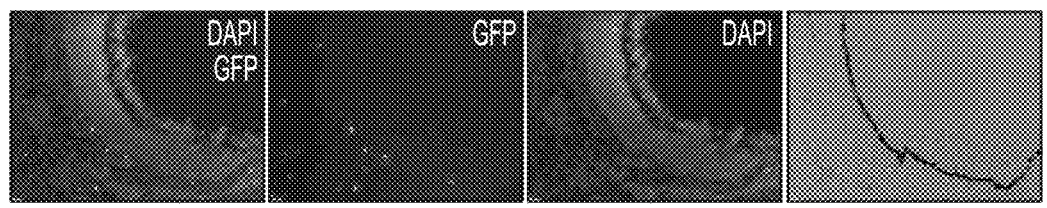
FIG. 6D
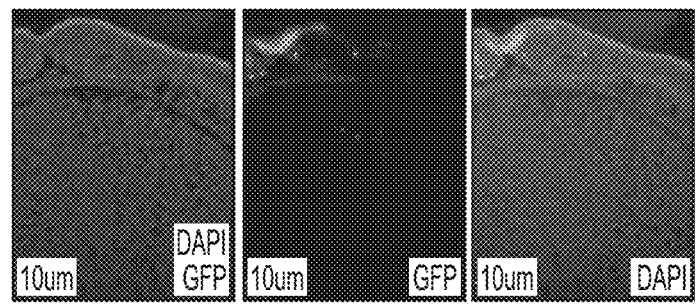
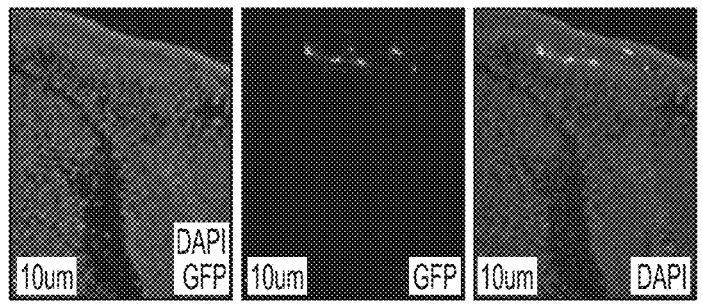
FIG. 6E

FUNCTIONAL MYELINATION OF NEURONS

CROSS REFERENCE TO RELATED APPLICATIONS

This application is a continuation of application Ser. No. 14/838,345, filed Aug. 27, 2015 which claims the benefit of provisional application 62/042,975, entitled "Functional Myelination of Neurons with Melanocyte Stem Cells," filed Aug. 28, 2014, the entire contents of which are incorporated herein.

STATEMENT OF GOVERNMENT INTEREST

This invention was made with government support under grant AR064810 awarded by the National Institutes of Health and under Project Number 1-I01BX002582 awarded by the United States Department of Veteran Affairs. The government has certain rights in the invention.

REFERENCE TO SEQUENCE LISTING SUBMITTED VIA EFS-WEB

This application includes an electronically submitted sequence listing in .txt format. The .txt file contains a sequence listing entitled "2015-11-13_15024-324US1_ST25.txt" created on Nov. 13, 2015 and is 4,373 bytes in size. The sequence listing contained in this .txt file is part of the specification and is hereby incorporated by reference herein in its entirety.

BACKGROUND

Destruction of the myelin sheath is a common theme in a wide range of neurological disorders, but the underlying causes are many fold. Demyelination may be immune-mediated, auto-antibody mediated, or caused by a demyelinating disease, trauma, toxins, bacterial infection, parasitic infection, viral infection, or genetic defect and can cause demyelination of neurites. This reduces the speed of neural transmission or stops it altogether. There is a need for improved therapies to restore functional myelination of demyelinated neurons.

Cholinergic treatments, such as acetylcholinesterase inhibitors (AChEIs), have been developed and may have beneficial effects on myelination, myelin repair, and myelin integrity. Increasing cholinergic stimulation also may act through subtle trophic effects on brain developmental processes and particularly on oligodendrocytes and the lifelong myelination process they support. Glycogen synthase kinase 3β inhibitors such as lithium chloride also have been found to promote myelination in mice with damaged facial nerves. Techniques have also been developed to include surgically implanting oligodendrocyte precursor cells in the central nervous system and inducing myelin repair with certain antibodies. While results with oligodendrocyte stem cell transplantation in mice have been encouraging, whether this particular technique can be effective in replacing myelin loss in humans is still unknown.

Melanocyte stem cells (MeSCs) are undifferentiated melanocytic precursor cells (MPCs) of the mammalian hair follicle (HF) responsible for recurrent generation of a large number of differentiated melanocytes during each HF cycle. To date, MeSCs have been studied most extensively in the mouse. Specifically, in murine skin, MeSCs reside within the bulge region of the resting hair follicle (HF), a continuous part of the outer root sheath that marks the bottom of the permanent portion of hair follicles.

SUMMARY

Embodiments of the invention include a method of isolating melanocyte stem cells from the hair follicle of mammalian skin to yield CD34(+) multipotent neural crest progenitor cells that can express myelin basic protein, comprising the steps of: (a) obtaining a suspension of skin cells that include MeSCs from the bulge region, the lower permanent portion, or both, of the hair follicle; (b) separating CD34(+) MeSCs from said single cell suspension; and (c) exposing said CD34(+) MeSCs to conditions that promote neural crest progenitor formation, to form CD34(+) multipotent neural crest progenitor cells that express the marker Gfap and express myelin basic protein.

In some embodiments, the conditions that promote neural crest progenitor formation comprise culturing said CD34(+) MeSCs in neural crest differentiation medium.

Further embodiments of the invention include isolated CD34(+) multipotent neural crest progenitor cells made according to the methods described above in this paragraph and throughout the specification. Preferably, the isolated CD34 (+) multipotent neural crest progenitor cells of embodiments of the invention are at least 80% pure, at least 85% pure, at least 90% pure, at least 95% pure, at least 97% pure, at least 98% pure, at least 99% pure, at least 99.5% pure, or at least 99.9% pure CD34(+) multipotent neural crest progenitor cells.

The cells of the invention and the methods described above in this paragraph and throughout the specification can involve isolated CD34(+) multipotent neural crest progenitor cells which are human cells, which are mouse cells, and which are mouse cells from a Dct-H2BGFP mouse. In addition, certain embodiments of the invention comprise a composition comprising an acceptable carrier and the isolated CD34(+) multipotent neural crest progenitor cells described above in this paragraph and throughout the specification. Certain embodiments of the invention also include substantially pure isolated CD34(+) multipotent neural crest progenitor cells from mammalian hair follicle bulge, and lower permanent portion of the hair follicle, which express the cell marker Gfap, and express myelin basic protein.

Embodiments of the invention also include a method of producing a dense myelin sheath around an axon, comprising contacting said axon with the isolated CD34(+) multipotent neural crest progenitor cells of the invention as described in the above paragraph and throughout the specification. This contacting can be and preferably is under conditions that promote myelination. Such conditions that promote myelination can comprise culturing said CD34(+) MeSCs in Poly-D-Lysine and Laminin-coated chambers in the presence of neural crest differentiation medium said medium; comprising 10 μM ascorbic acid to induce myelination.

Additional embodiments of the invention include a method of producing a functional myelin sheath on an axon which lacks a functional myelin sheath or has become demyelinated, comprising contacting said axon with the isolated CD34(+) multipotent neural crest progenitor cells described in the above paragraph and throughout the specification. Such contacting can be administration by direct injection into the area of said axon, or by intrathecal injection, or intravenously, or by stereotaxic injection, including in the central nervous system, the peripheral nervous system, or both.

Embodiments of the invention include where the demyelination of said axon is immune-mediated, auto-antibody mediated, or caused by a demyelinating disease, trauma, toxin, bacterial infection, viral infection, parasitic infection, or genetic defect, and where said demyelinating disease is selected from the group consisting of: experimental allergic encephalomyelitis, acute disseminated encephalomyelopathy, acute hemorrhagic encephalomyelopathy, experimental allergic neuritis, amoebic meningoencephalitis, Guillain-Barre syndrome, multiple sclerosis, stroke, traumatic brain injury, and traumatic peripheral nerve injury, Devic's disease (otherwise known as neuromyelitis optica (NMO)), NMO spectrum disorder, progressive multifocal leukoencephalopathy, central pontine myelinolysis, Tabes dorsalis, optic neuritis, transverse myelitis, progressive inflammatory neuropathy, myelopathy, chronic inflammatory demyelinating polyneuropathy, Charcot-Marie-Tooth disease, visna, and the like.

These and other features, aspects, and advantages of the present invention will become better understood with regard to the following description, appended claims, and accompanying figures.

BRIEF DESCRIPTION OF THE DRAWINGS

The following drawings form part of the present specification and are included to further demonstrate certain embodiments of the present invention. The invention may be better understood by reference to one or more of these drawings in combination with the detailed description of specific embodiments presented herein.

FIG. 1A-1E are photographs showing the identification of GFP-expressing melanocyte precursor cells in bulge/LPP and SHG of telogen HF. Distinct subpopulations of GFP-expressing cells in the CD34(+) bulge/LPP region (arrows, FIG. 1A) and P-Cad$^+$ SHG region (arrows, FIG. 1B) in P56 dorsal skin HFs are shown. FIG. 1C: Co-localization of Kit protein expression and GFP-expressing cells from both bulge/LPP and SHG (arrows). Inset boxes show higher magnification of an individual GFP-expressing cell co-localizing with c-Kit expression. FIG. 1D: Co-localization of Dct expression and GFP-expressing cells from both bulge/LPP and SHG (arrows). Inset boxes show higher magnification of individual GFP-expressing cell co-localizing with Dct expression. FIG. 1E: GFP-expressing cells and anti-CD34 immunofluorescence in P56 dorsal skin HF. The arrows point out co-localization of bulge/LPP GFP-expressing cell and CD34 expression and the arrowheads show that SHG GFP-expressing cells lack CD34 expression. Col IV staining outlines the HF border.

FIG. 2A-2C are photographs and graphs illustrating the separation of bulge/LPP and SHG GFP-expressing melanocyte precursor cells of telogen HFs. FIG. 2A: is an experimental scheme where MeSCs identified in HF bulge/LPP and SHG of Dct-H2BGFP mice were separated using fluorescence activated sorting (FACS) with GFP and anti-CD34. FIG. 2B: shows the separation of bulge/LPP (CD34(+) GFP$^+$), SHG (CD34$^-$GFP$^+$) melanocyte precursor cells and (CD34(+)GFP$^-$), (CD34$^-$GFP$^-$) dermal cells using FACS with GFP and anti-CD34, showing a representative image of the FACS. FIG. 2C illustrates quantitative RT-PCR analysis for the expression of Dct, Krt14, Cdh3, and Cd34 genes among the CD34(+)GFP$^+$(bulge), CD34$^-$ GFP$^+$(SHG), CD34(+)GFP$^-$ and CD34$^-$GFP$^-$ sorted cell populations. (*P≤0.01 by ANOVA).

FIG. 3A: quantitative RT-PCR analysis for the expression of Tyr, Tyrp1 and Pmel among the bulge/LPP (CD34(+)GFP$^+$) and SHG (CD34(+)GFP$^+$) sorted cells. FIG. 3B: In vitro melanocyte differentiation potential of CD34(+)GFP$^+$ (bulge) and CD34$^-$GFP$^+$ (SHG) MeSCs in melanocyte differentiation culture condition for 4 days (top two panels) or 7 days (bottom two panels). FIG. 3C: Quantitation data of the bulge/LPP and SHG melanocyte precursor cell potential to produce pigmented melanocytes in melanocyte differentiation medium at the 4$^{th}$ and 7$^{th}$ day. (*P≤0.01).

FIG. 4A: Formation of non-adherent spheroids was studied among CD34(+)GFP$^+$ (bulge/LPP) melanocyte precursors and CD34$^-$GFP$^+$ (SHG) cells when cultured in neural crest stem cell medium for up to 8 days (top panels). The image in the bottom panel depicts retention of GFP expression in spheroids formed by both cell types. FIG. 4B: The size of non-adherent spheroids derived from bulge/LPP and SHG MeSCs when cultured in neural crest stem cell medium as determined at days 2, 4, 6 and 8 day. (*P≤0.01). FIG. 4C: Expression of neural crest lineage markers Gfap, α-Sma, Tuj1, Krt15 among CD34(+)GFP$^+$ (bulge) (top panel) and CD34$^-$GFP$^+$ (SHG) (bottom panel) MeSCs following adherent culture in neural crest differentiation medium. FIG. 4D: Expression of melanocyte lineage marker Tyrp1 among CD34(+)GFP$^+$ (bulge) (top panel) and CD34$^-$GFP$^+$ (SHG) (bottom panel) MeSCs following adherent culture in melanocyte differentiation medium. In the right two panels, brightfield images show pigmented melanocytes among cultured CD34(+)GFP$^+$ (bulge) (top) and CD34$^-$GFP$^+$ (SHG) (bottom) MeSCs. FIG. 4E: Quantitation of neural crest-derived cell and melanocyte marker expression frequency after cells were cultured in either neural crest differentiation (left) or melanocyte differentiation (right) condition.

FIG. 5A: Schematic of in vitro dorsal root ganglion (DRG) co-culture system: For this experiment, embryonic DRGs from rat at E17 (Lonza) or DRGs from myelin-deficient neonatal P5 shi/shi mice were isolated. DRG cells were cultured for one week on Poly-D-Lysine and laminin-coated 24-well plates to develop neurites. CD34(+) or CD34(−)MeSCs isolated from Dct-H2BGFP mouse skin or rat oligodendroglial cells (ODC) were then seeded onto the dense neuronal bed. After one week of co-culture, cells were fixed and studied for myelination of axons by immunofluorescence for the expression of myelin basic protein (Mbp) or determining the presence or absence of myelin sheath formation by electron microscopy. FIG. 5B: Co-cultures of CD34(+) or CD34(−) MeSCs and rat embryonic DRGs. In the image, the arrows point to GFP-expressing cells, the solid arrows representing CD34(+) bulge/LPP MeSCs and the dotted arrows representing CD34(−)SHG MeSCs in the DRG co-cultures. The second and fourth rows are high magnification images of their respective lower magnification top row images. FIG. 5C: The top row depicts Mbp expressed by ODCs (left panel) and Tuj1 expressed by Shiverer axonal outgrowths (center). In the bottom row, high magnification images of the region marked with a white box are shown; it depicts MBP deposition along a Tuj1-expressing Shiverer axon. FIG. 5D: Co-cultures of CD34(+) or CD34(−)MeSCs, or DRGs alone with no added cells, and neonatal Shiverer DRGs. In the image, the arrows point to GFP-expressing cells, the solid arrows representing CD34(+) bulge/LPP MeSCs and the dotted arrows representing CD34(−)SHG melanocyte precursor cells in DRG co-cultures. FIG. 5E: Electron-dense myelin sheath formation around Shiverer neurites when co-cultured with CD34(+) or CD34(−)MeSCs or no cells using electron microscopy. At the right side in either CD34 (+) or CD34(−) MeSCs co-cultured with Shiverer DRGs, high magnification images of the region marked with black box are shown. In the case where no cells were co-cultured with Shiverer DRGs, the right image is a high magnification of the left image.

FIG. 6A-6E are photographs providing a characterization of the Dct-Tta$^{KT}$H2b-Gfp bitransgenic mouse model. FIG. 6A shows the expression of H2BGFP in embryonic melanoblast, in the trunk and sub- and supra-optic region at E12.5. Post-natal H2BGFP in melanocyte cells of skin hair follicles is shown in FIG. 6B (anagen) and FIG. 6C (telogen). Expression of H2BGFP in embryonic melanoblasts (E12.5) are shown in the cross section of the eye (FIG. 6D) and in the spinal cord (FIG. 6E). FIG. 6E shows two representative sets of three images.

In FIG. 8A, GFP-expressing cells were quantitated within and outside of the hair follicles of Dct-Tta$^{KT}$H2b-Gfp mouse skin based on staining of Col IV, which marks the basement membrane or border of hair follicles. Images in the top panel of FIG. 8A represent GFP-expressing cells within, outside, and on the border of each hair follicle visualized. The bottom panel of FIG. 8A is a schematic representation of GFP-expressing cells depicted as bulge/LPP(*) and SHG (−). FIG. 8B is a table showing quantitation of GFP-expressing cells from the bulge/LPP and the SHG compartments of hair follicles in three different categories, by location within, outside, or on the border of the hair follicles.

In FIG. 12A, two individual litters were screened for two individual repeats in the top and bottom panels of the figure, for genotyping to identify Mbp(+) Shiverer pups, which were further used to isolate dorsal root ganglia at P5 to P8. FIG. 12B shows a representative image for GFP-expressing cells CD34(+) or CD34(−) or No cells) co-cultured along the side of neurites generated from dorsal root ganglia isolated from Shiverer pups. After the identification of samples for GFP-expressing cells in their representative cultures, the samples were fixed and sent for electron microscopy.

DETAILED DESCRIPTION

Figure 3A:
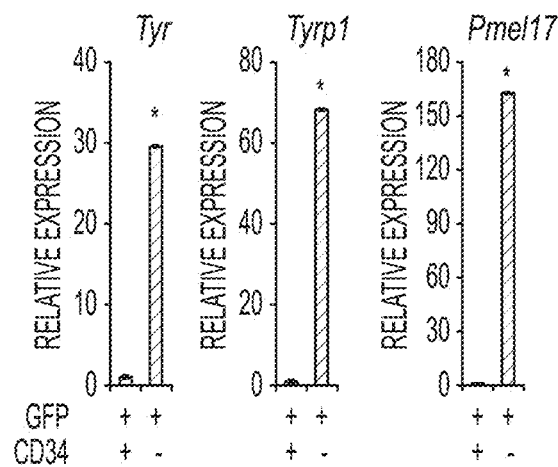
FIG. 3A-3C are photographs and bar graphs representing distinct melanogenic properties of bulge/LPP_and SHG melanocyte precursor cells of telogen HFs.

Undifferentiated MeSCs residing in the bulge/LPP region and the secondary hair germ (SHG) regions of the mammalian HF can be separated into two distinct molecular and functional classes that are distinguished by their mutually exclusive expression of CD34. MeSCs that express CD34 or "CD34(+) MeSCs" are isolated from MeSCs from the bulge/LPP region/LPP of the HF and express high levels of CD34. These cells have a broader differentiation potential compared with MeSCs that do not express CD34, or "CD34 (−) MeSCs." Of particular interest are CD34(+) MeSCs that represent a more primitive and multipotent subset of MeSCs.

It has been discovered that when these CD34(+) MeSCs are co-cultured with myelin-deficient DRG neurites (that lack a functional myelin sheath) under conditions that promote neural crest progenitor formation, upon differentiation, the resulting CD34(+) multipotent neural crest progenitor cells express the marker Gfap and myelin basic protein (Mbp) along axons and to form a dense, multilayered myelin sheath. Accordingly, these CD34(+) multipotent neural crest progenitor cells derived from MeSCs from the HF bulge/LPP region can be used for generation of a dense myelin sheath as well as therapeutically for demyelinating diseases, such as multiple sclerosis and optic neuritis.

In the following description, for the purposes of explanation, numerous specific details are set forth in order to provide a thorough understanding of the present invention. It will be apparent, however, to one skilled in the art that the present invention may be practiced without these specific details. In order that the invention may be readily understood and put into practical effect, particular preferred embodiments will now be described by way of the following non-limiting examples.

1. DEFINITIONS

Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described below. However, the skilled should understand that the methods and materials used and described are examples and may not be the only ones suitable for use in the invention. Moreover, it should also be understood that as measurements are subject to inherent variability, any temperature, weight, volume, time interval, pH, salinity, molarity or molality, range, concentration and any other measurements, quantities or numerical expressions given herein are intended to be approximate and not exact or critical figures unless expressly stated to the contrary. Hence, where appropriate to the invention and as understood by those of skill in the art, it is proper to describe the various aspects of the invention using approximate or relative terms and terms of degree commonly employed in patent applications, such as: so dimensioned, about, approximately, substantially, essentially, consisting essentially of, comprising, and effective amount.

Generally, nomenclature used in connection with, and techniques of, cell and tissue culture, molecular biology, immunology, microbiology, genetics, protein, and nucleic acid chemistry and hybridization described herein are those well-known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lan, Antibodies: A Laboratory Manual, Cold Spring Harbor Laboratory Press, Cold Spring Harbor, N.Y. (1990); Principles of Neural Science, 4th ed., Eric R. Kandel, James H. Schwartz, Thomas M. Jessell editors. McGraw-Hill/Appleton & Lange: N.Y., N. Y. (2000). Unless defined otherwise, all technical and scientific terms used herein have the same meaning as commonly understood by one of ordinary skill in the art.

The term "administering" as used herein, means delivery, for example of a CD34+ multipotent neural crest progenitor cell.

The term "bulge region/lower permanent portion" as used herein, refers to an anatomical location in the outer root sheath at and below the insertion point of the arrector pili muscle of the hair follicle. The "lower permanent portion" (LPP) is synonymous with the bulge in the mouse hair follicle. This term is used to distinguish it from the secondary hair germ (SHG), where CD34(−) MeSCs are found, and is a structure that disappears during certain phases of the hair follicle growth cycle. It houses several types of stem cells, which supply the entire hair follicle with new cells. These stem cells develop in situ into epithelial cells and melanocytes. Melanocyte stem cells have been identified in the bulge/LPP and secondary hair germ compartment of telogen HFs.

The term "CD34(+) melanocyte stem cell" or "CD34(+) MeSC" as used herein, means a subset of undifferentiated MeSCs in mouse HFs which express the membrane protein CD34 and have the ability to differentiate into cells of neural crest lineage that express at least the cell markers Gfap and Mbp.

The term "CD34(−) melanocyte stem cell" or "CD34(−) MeSC" as used herein, means a subset of undifferentiated MeSCs in mouse HFs which do not express CD34 and have the ability to differentiate as a melanocyte cell but not cells of a glial lineage.

The term "contacting" as used herein, means bringing into close physical association or immediate proximity, including physically touching. For example, "contacting" can include exposing the extracellular surface of a demyelinated axon with solution or suspension containing cells.

The term "Dct-H2BGFP$^{KI}$ mouse" or "Dct-Tta$^{KI}$H2b-GFP" or "DCT-H2BGFP" as used herein, is a knock-in mouse model expressing the tetracycline-regulated transactivator (tTA) gene under the control of the murine dopachrome tautomerase (Dct) melanocyte specific promoter to allow a melanocyte specific tTA transactivation in vivo and designed to drive expression of H2BGFP constitutively in bitransgenic Dct-tTA knock-in-TRE-H2BGFP mice in the absence of doxycycline.

The term "demyelination" as used herein, means damage to the myelin sheath around nerve process, or its absence.

The term "demyelinating disease" as used herein, means any condition that results in damage to or absence of the protective covering (myelin sheath) that surrounds nerve fibers in the brain and spinal cord, or in the peripheral nervous system. When the myelin sheath is damaged, nerve impulses slow or even stop, causing neurological problems.

The term "detectable" refers to any amount that can be discerned by an assay or measurement system known to a person of skill in the art, above background, to a degree of statistical certainty, for example a P value of ≤0.05 as a measure of statistical significance or to any level suitable for the analysis being conducted according to standards acceptable to the person of skill in the art.

The term "dorsal root ganglion," (or spinal ganglion) (also known as a posterior root ganglion), as used herein, means a cluster of nerve cell bodies (a ganglion) in a posterior root of a spinal nerve.

The term "exposing" when referring to exposing to conditions that promote neural crest progenitor formation, refers to subjecting to any environment under which neural crest progenitors are formed, or under which a stem cell differentiates or partially differentiates to form a lineage of cells derived from neural crest progenitors. Thus, the term includes subjecting to any condition wherein cells, including MeSCs, have or gain the capacity to differentiate into neural or glial cell types, including myelin basic protein-expressing cells, myelin depositing cells, glia or Schwann cells. Such conditions can be in vitro or in vivo.

The terms "express," "expression," and "expressing," as used herein with respect to gene products, indicate that the gene product of interest is produced by the cell at a detectable level. "Significant expression" refers to expression of the gene product of interest to 10% above the minimum detectable expression. Cells with "high expression" or "high levels" of expression of a given expression product are the 10% of cells in a given sample or population of cells that exhibit the highest expression of the expression product. Cells with "low expression" of a given expression product are the 10% of cells in a given sample or population of cells that exhibit the lowest expression of the expression product (which can be no expression).

The term "hair follicle" is used according to the usual meaning in the art, and includes skin appendages of the vertebrate skin, preferably mammalian skin, that have the ability to periodically and stereotypically regenerate in order to continuously produce new hair over a lifetime. The term is contemplated to refer to any hair follicle of any vertebrate, preferably a mammal, including human and mouse hair follicles, as well as any research, working or companion mammal.

The terms "isolated," "isolating," "purified," "purifying," "enriched," and "enriching," as used herein with respect to cells, means that the MeSCs at some point in time were separated and sorted to produce two subsets: CD34(+) MeSCs and CD34(−) MeSCs both of which are capable of directed differentiation. "Highly purified," "highly enriched," and "highly isolated," when used with respect to cells, indicates that the cells of interest are at least about 70%, about 75%, about 80%, about 85% about 90% or more of the cells, about 95%, at least 99% pure, at least 99.5% pure, or at least 99.9% pure or more of the cells, and can preferably be about 95% or more of the differentiated cells.

The term "melanocyte stem cell," or "MeSC" as used herein, refers to undifferentiated stem cells residing within the bulge and/or lower permanent portion and/or SHG region of the mammalian HF. In situ, these cells are responsible for pigment regeneration during recurrent HF cycles.

The term "myelin" as used herein, refers to a fatty white insulating substance that surrounds neuronal processes, forming in multiple layers, the "myelin sheath," usually around only the axon of a neuron. It is essential for the proper functioning of the nervous system and is an outgrowth of a type of glial cell sometimes referred to as Schwann cells. A functional myelin sheath is a densely applied layer of fatty membrane which increases transmission in a neuronal projection or axon to which it is applied.

The term "myelin basic protein" as used herein, refers to a protein important in the process of myelination of nerves in the nervous system. The myelin sheath is a multi-layered membrane, unique to the nervous system that functions as an insulator to greatly increase the velocity of axonal impulse conduction.

The term "neurite," as used herein, means any projection from the cell body of a neuron. This projection can be either an axon or a dendrite, particularly in its undifferentiated stage. In certain embodiments, the "neurite" preferably is an axon.

The term "neuron," as used herein, means an electrically excitable cell that processes and transmits information through electrical and/or chemical signals. These signals between neurons occur via synapses, specialized connections with other cells. Neurons can connect to each other to form neural networks. Neurons are the core components of the brain and spinal cord of the central nervous system (CNS), and of the ganglia of the peripheral nervous system (PNS). Specialized types of neurons include: sensory neurons which respond to touch, sound, light and all other stimuli affecting the cells of the sensory organs that then send signals to the spinal cord and brain, motor neurons that receive signals from the brain and spinal cord to cause muscle contractions and affect glandular outputs, and interneurons which connect neurons to other neurons within the same region of the brain, or spinal cord in neural networks. A typical neuron consists of a cell body (soma), dendrites, and an axon.

The term "population" as used herein when used with respect to cells, means a group or collection of cells that share one or more characteristics. The term "subpopulation," when used with respect to cells, refers to a population of cells that are only a portion or "subset" of a population of cells.

The term "acceptable carrier" as used herein, means excipients, emollients, and stabilizers or stabilizing agents or other acceptable materials, compositions, or structures involved in holding, carrying, transporting, or delivering any subject cell or composition. Each means must be "acceptable" in the sense of being compatible with the other ingredients of a subject composition and not injurious to the subject.

The term "multipotent" as used herein, refers to a property of any stem cell or progenitor cell, meaning that it has the ability to differentiate into two or more different cell types. The term includes totipotent, pluripotent, oligopotent and bipotent. It therefore describes a property of both embryonic stem cells and adult stem cells, any of which can divide through mitosis to produce more stem cells and can differentiate into two or more specialized cells. A "multipotent neural crest progenitor cell refers to a cell that has the capacity to differentiate into cells of at least the neural crest lineage, which includes any of the diverse cells of the neural crest, including but not limited to melanocytes, craniofacial cartilage, craniofacial bone, smooth muscle, peripheral neurons, enteric neurons, and glia, including Schwann cells.

The term "remyelination" as used herein means the regenerative process by which a demyelinated axon is reinvested with a new myelin sheath. It is associated with functional recovery and maintenance of axonal health. It can occur as a spontaneous regenerative response following demyelination in a range of pathologies including immune-mediated, auto-antibody mediated, or caused by a demyelinating disease, trauma, toxin, bacterial infection, viral infection, parasitic infection, or genetic defect.

The term "Schwann cells" or "SCs" are a type of cell found throughout the entire peripheral nervous system (PNS). The PNS includes all nerves going out to muscles as well as sensory nerves coming from the muscles back to the spinal cord. Schwann cells are a type of "support" cell in the PNS. Schwann cells myelinate individual nerve fibers (e.g., axons), which is necessary for sending appropriate electrical signals throughout the nervous system. Schwann cells are not stem cells. They are adult cells and can only be Schwann cells in their natural environment. Schwann cells are absolutely essential for regeneration in the injured PNS.

The term "single cell suspension" as used herein, means tissue broken up into single cells suspended in a liquid of some type as opposed to clumps of cells or tissue attached to each other by extra cellular matrix.

The terms "subject," "host," and "patient," as used herein, are used interchangeably and mean a mammalian animal being treated with the present compositions, including, but not limited to, vertebrates, simians, humans, felines, canines, equines, rodents (including rats, mice and the like), bovines, porcines, ovines, caprines, mammalian farm animals, mammalian sport animals, and mammalian pets.

The terms "substantially pure," "substantially purified," and "substantially enriched" as used herein with respect to cells means the isolated cell population of mammalian melanocyte stem cells that includes at least 80% pure, and preferably at least 85% pure, at least 90% pure, at least 95% pure, at least 97% pure, at least 98% pure, at least 99% pure, at least 99.5% pure, or at least 99.9% pure cells of the type in question, for example, CD34(+) multipotent neural crest progenitor cells.

The term "skin-derived precursors" or "SKPs" as used herein means an endogenous multipotent precursor cell present in human skin that can be isolated and expanded and differentiated into both neural and mesodermal cell types. SKPs share characteristics with, and have multipotentiality similar to, embryonic neural crest stem cells. SKPs derive from endogenous adult dermal precursors that exhibit properties similar to embryonic neural-crest stem cells.

As used herein, a "therapeutic agent" means a compound or molecule capable of producing an effect. Preferably, the effect is beneficial.

As used herein, "therapeutically effective amount" means an amount sufficient to treat a subject afflicted with a demyelination which is immune-mediated, auto-antibody mediated, due to a demyelinated disease, or due to trauma, a toxin, a viral infection a bacterial infection, or genetic defect to alleviate a symptom or a complication associated with the disease.

The term "treating" as used herein, means slowing, stopping, or reversing the effects of a demyelination, or causing remyelination or partial remyelination, when demyelination is immune-mediated, auto-antibody mediated, due to a demyelinated disease, or due to trauma, a toxin, a viral infection, a bacterial infection, a parasitic infection, or genetic defect. As used herein, the terms "treatment," "treating," and the like, as used herein refer to obtaining a desired pharmacologic and/or physiologic effect. The effect may be prophylactic in terms of completely or partially preventing a condition or disease or symptom thereof and/or may be therapeutic in terms of a partial or complete cure for a condition or disease and/or adverse effect attributable to the condition or disease. "Treatment," includes any treatment of a condition or disease in a mammal, particularly in a human, and includes: (a) preventing the condition or disease or symptom thereof from occurring in a subject which may be predisposed to the condition or disease but has not yet been diagnosed as having it; (b) inhibiting the condition or disease or symptom thereof, such as, arresting its development; and (c) relieving, alleviating or ameliorating the condition or disease or symptom thereof, such as, for example, causing regression of the condition or disease or symptom thereof.

2. BACKGROUND

Neural Crest

Stem cells are defined by their ability to both self-renew and give rise to multiple lineages in vivo and/or in vitro. The embryonic neural crest is a multipotent tissue that gives rise to a plethora of differentiated cell types in the adult organism and is unique to vertebrate embryos. The neural crest is an ideal source for multipotent adult stem cells. The neural crest is derived from the ectoderm but has sometimes been called the fourth germ layer because of its importance. The neural crest cells originate at the dorsal most region of the neural tube. The neural crest cells migrate extensively to generate a prodigious number of differentiated cell types. These cell types include (1) the neurons and glial cells of the sensory, sympathetic, and parasympathetic nervous systems, (2) the epinephrine-producing (medulla) cells of the adrenal gland, (3) the pigment-containing cells of the epidermis, and (4) many of the skeletal and connective tissue components of the head. The fate of the neural crest cells depends, to a large degree, on where they migrate to and settle. Significant advances have been made in the past few years isolating neural crest stem cell lines that can be maintained in vitro and can give rise to many neural crest derivatives either in vitro or when placed back into the context of an embryo.

Schwann Cells

The myelinating Schwann cells in peripheral nerves are derived from the neural crest. Schwann cell development occurs through a series of transitional embryonic and postnatal phases, which are tightly controlled by a number of signals. During the early embryonic phases, neural crest cells are specified to give rise to Schwann cell precursors. These SCPs the first transitional stage in the Schwann cell lineage, and then generate the immature Schwann cells. At birth, the immature Schwann cells differentiate into the myelinating Schwann cells that populate the mature nerve trunks. See Woodhoo, A. "Development of the Schwann Cell Lineage: From the Neural Crest to the Myelinated Nerve." GLIA 56:1481-1490 (2008).

Schwann cells have been proposed for a number of clinical applications based on their ability to remyelinate demyelinated lesions (Blakemore and Crang, 1985; Kohama et al., 2001) and to promote regeneration and remyelination in the injured spinal cord (Takami et al., 2002; Pearse et al., 2004). Schwann cells which are the principal glial cells of the peripheral nervous system, and myelinate individual nerve fibers (e.g., axons), which is necessary for sending appropriate electrical signals throughout the nervous system. They can be dedifferentiated in vitro to a glia/melanocyte precursor. Melanocytes and glia can be derived from a common bipotent neural crest precursor.

3. OVERVIEW

MeSCs residing in the bulge/LPP region of the HF and the secondary hair germ (SHG) regions of the mammalian HF can be separated into two distinct molecular and functional classes that are distinguished by their mutually exclusive expression of CD34. CD34 expressing MeSCs known as CD34(+) MeSCs isolated from MeSCs in the bulge/LPP region of the HF exhibit express high levels of CD34. CD34(+) MeSCs have a broader differentiation potential compared with non-CD34 expressing cells known as CD34 (−) MeSCs. Of particular interest are CD34(+) MeSCs that represent the more primitive subset of the MeSCs. It has been discovered that these CD34(+) MeSCs, under conditions that promote neural crest progenitor formation and ultimately myelination, form cells that express at least one of the markers Gfap, Mbp, α-Sma, Tuj1, Krt15, and nestin. These CD34(+) multipotent neural crest progenitor cells have the ability to produce a functional, dense, multilayered myelin sheath on neuronal axons.

Without being bound by theory, the observation that, in one example, a loose myelin sheath was observed in a co-culture of CD34(−) MeSCs with shi/shi neurites may suggest either that a subset of these CD34(−) MeSCs possess a limited ability to generate a myelin sheath, that these CD34(−) MeSCs were incompletely separated from CD34 (+) MeSCs, or that a cell surface protein not yet identified will be more optimal than CD34 for identifying which CD34(+) multipotent neural crest progenitor cells selectively possess glial potential.

Mouse and human SKPs isolated non-specifically from mammalian dermis possess similar molecular and cellular differentiation properties of the highly-specific, CD34(+) multipotent neural crest progenitor cells that now have been found to differentiate from CD34(+) MeSCs that were isolated from the MeSCs found in the HF bulge/LPP. CD34 (+) expression can be detected in a subset of human skin SKPs. The discovery of the unique differentiation properties of CD34(+) MeSCs indicates that human SKPs with this ability can be isolated and used therapeutically for demyelinating diseases, including, but not limited to, multiple sclerosis and optic neuritis. Furthermore, CD34(+) MeSCs can be used as a discovery tool for markers of highly-specific human skin-derived stem cell subsets that can be leveraged for these therapeutic purposes.

4. EMBODIMENTS

The CD34(+) MeSCs subject to conditions that promote neural crest progenitor formation are able to form CD34(+) multipotent neural crest progenitor cells that express at least one of the markers Gfap, Mbp, α-Sma, Tuj1, Krt15 and nestin. They also have the ability to produce a functional, dense, multilayered myelin sheath on neuronal axons. Accordingly, methods of making these isolated MeSCs comprising these CD34(+) multipotent neural crest progenitor cells, compositions and kits comprising them, are provided. Methods for producing a dense myelin sheath around the neurite are also provided.

A. Methods of Isolating MeSCs to Yield CD34(+) Multipotent Neural Crest Progenitor Cells Certain embodiments described herein relate to methods of isolating MeSCs from the mammalian skin HF to yield CD34(+) multipotent neural crest progenitor cells that can express at least one of the markers Gfap, Mbp, α-Sma, Tuj1, Krt15, and nestin. The method includes obtaining a suspension of skin cells that includes MeSCs from the bulge/LPP region, the lower permanent portion, or both, of the hair follicle. Then, CD34(+) MeSCs are separated from the single cell suspension. The CD34(+) MeSCs are then exposed to conditions that promote neural crest progenitor formation to form CD34(+) multipotent neural crest progenitor cells that express at least one of the markers Gfap, Mbp, α-Sma, Tuj1, Krt15, and nestin.

In a preferred embodiment, the method comprises preparing a cell suspension from mammalian dermal tissue comprising HFs. Such a cell suspension generally comprises CD34(+) MeSCs and CD34(−) MeSCs. CD34(+) MeSCs are separated from the cell suspension using any convenient method known in the art, for example, a fluorescence-based sorting techniques and expression labels. Suitable labels include, but are not limited to green fluorescent protein (GFP), varieties of other fluorescent proteins including yellow and red, other optical labels utilized for cell separation whose expression is driven by the Dct promoter, CD34, or other cell surface markers whose expression is highly correlated with the expression of GFP or its derivatives, or CD34, or both. Anti-CD34 antibody is preferred to specifically label the CD34(+) MeSCs to produce CD34(+) multipotent neural crest progenitor cells.

Techniques for labeling, sorting, fluorescence activated cell sorting (FACS), and enrichment of cells are well known in the art. Useful examples are described in WO 2001/022507 and U.S. application Ser. No. 13/391,251 (US 2012-0220030 A1), which are hereby incorporated by reference in their entirety, and specifically for their description of cell labeling, sorting, and enrichment. The cells can be identified, separated, and/or enriched based on cell markers. It will be understood by those of skill in the art that the stated expression levels reflect detectable amounts of the marker protein on the cell surface. Generally, cell markers can be assessed by staining or labeling cells with probes that specifically bind the marker of interest and that generate a detectable signal.

CD34(+) MeSCs and CD34(−) MeSCs were subjected to gene expression and in vitro cell culture studies for assessment of their neural crest lineage potential as well as the melanogenic properties of CD34(+) multipotent neural crest progenitor cells and their ability to myelinate axons. Sorted CD34(+) MeSCs and CD34(−) MeSCs were counted and used either for primary cultures or for quantitative real-time PCR (qRT-PCR) by extracting RNA from respective cell populations. In preferred embodiments, molecular techniques such as quantitative RT-PCR were used to show high levels of Dct and low levels of Krt14 expression in bulge/LPP and SHG isolated multipotent neural crest progenitor cells. Cdh3 (P-cadherin, a SHG compartment marker) is high only in CD34(−) GFP(+)multipotent neural crest progenitor cells.

Biological properties of both CD34(+) and CD34(−) multipotent neural crest stem cells were determined by introducing the CD34(+) MeSCs and CD34(−) MeSCs in melanocyte differentiation conditions for a period of seven days. Recipes for media can vary in pH, glucose concentration, growth factors, and the presence of other nutrients. Classically, the control of stem cell fate has been attributed to genetic and molecular mediators (growth factors, cytokines, and transcription factors). Useful examples of melanocyte differentiation conditions are described in "Culture of human melanocytes. Its contribution to the knowledge of melanocyte physiology," Pathol Biol (Paris) 1992 February; 40 (2): 114-20 and "In Vitro Dedifferentiation of Melanocytes from Adult Epidermis," PLOS, published Feb. 23, 2001. Culture conditions vary widely for each cell type, but the artificial environment in which the cells are cultured invariably consists of a suitable vessel containing the following: (i) a substrate or medium that supplies the essential nutrients (amino acids, carbohydrates, vitamins, minerals). (ii) growth factors, (iii) hormones, (iv) gases ($O_2$, $CO_2$), and (v) a regulated physico-chemical environment (pH, osmotic pressure, temperature). One of ordinary skill in the art could readily optimize the differentiation conditions.

In preferred embodiments, these conditions included plating the cells in 24-well plates with melanocyte differentiation inducing culture medium containing 5% fetal bovine serum (FBS), 50 ng/ml stem cell factor (SCF), 20 nM endothelin-3, 2.5 ng/ml basic fibroblast growth factor (FGF), 100 nM α-melanocyte stimulating hormone (α-MSH), 1 μM phosphoethanolamine, 10 μM ethanolamine, 1 mg/mL insulin and 1% penicillin/streptomycin in RPMI 1640 medium. Notably, CD34(−) MeSCs formed dendritic structures and produced new pigmented melanocytes, while CD34(+) MeSCs did not. The data suggest CD34(−) MeSCs possess significantly higher potential to produce pigmented melanocytes relative to bulge/LPP cells in melanocyte differentiation medium. Based on molecular and biological properties, the CD34(−) melanocyte stem cells under these conditions produced more advanced states of melanocyte differentiation whereas notably, CD34(+) MeSCs represent a primitive neural crest cell state.

Melanocytes are neural crest derived cells. The CD34(+) MeSCs and CD34(−) MeSCs were introduced into neural crest stem cell medium. Useful examples for generating neural crest stem cell medium are described in Bixby S. et al., 2002 and in Pfaltzgraff E R et al., 2012. One of ordinary skill in the art could readily determine the necessary components and percentages of components in an effort to optimize the medium to desired experimental protocols. As set forth below, a person of ordinary skill in the art having knowledge of the components of these type of media could optimize different concentrations of the components to arrive at desired medium including nutrients needed for long-term growth of cells.

DMEM (Dulbecco's Modified Eagle Medium)
Composition of Neurobasal medium

| Components | Concentration (mg/L) |
|---|---|
| Amino Acids | |
| Glycine | 30.0 |
| L-Alanine | 2.0 |
| L-Arginine hydrochloride | 84.0 |
| L-Asparagine-H2O | 0.83 |
| L-Cysteine | 31.5 |
| L-Histidine hydrochloride-H2O | 42.0 |
| L-Isoleucine | 105.0 |
| L-Leucine | 105.0 |
| L-Lysine hydrochloride | 146.0 |
| L-Methionine | 30.0 |
| L-Phenylalanine | 66.0 |
| L-Proline | 7.76 |
| L-Serine | 42.0 |
| L-Threonine | 95.0 |
| L-Tryptophan | 16.0 |
| L-Tyrosine | 72.0 |
| L-Valine | 94.0 |
| Vitamins | |
| Choline chloride | 4.0 |
| D-Calcium pantothenate | 4.0 |

-continued

| Components | Concentration (mg/L) |
| --- | --- |
| Folic Acid | 4.0 |
| Niacinamide | 4.0 |
| Pyridoxal hydrochloride | 4.0 |
| Riboflavin | 0.4 |
| Thiamine hydrochloride | 4.0 |
| Vitamin B12 | 0.0068 |
| i-Inositol | 7.2 |
| Inorganic Salts | |
| Calcium Chloride (CaCl2) (anhyd.) | 200.0 |
| Ferric Nitrate (Fe(NO3)3"9H2O) | 0.1 |
| Magnesium Chloride (anhydrous) | 77.3 |
| Potassium Chloride (KCl) | 400.0 |
| Sodium Bicarbonate (NaHCO3) | 2200.0 |
| Sodium Chloride (NaCl) | 3000.0 |
| Sodium Phosphate monobasic (NaH2PO4—H2O) | 125.0 |
| Zinc sulfate (ZnSO4—7H2O) | 0.194 |
| Other Components | |
| D-Glucose (Dextrose) | 4500.0 |
| HEPES | 2600.0 |
| Phenol Red | 8.1 |
| Sodium Pyruvate | 25.0 |

Composition of B-27 supplement

| Components |
| --- |
| Vitamins |
| Biotin |
| DL Alpha Tocopherol Acetate |
| DL Alpha-Tocopherol |
| Vitamin A (acetate) |
| Proteins |
| BSA, fatty acid free Fraction V |
| Catalase |
| Human Recombinant Insulin |
| Human Transferrin |
| Superoxide Dismutase |
| Other Components |
| Corticosterone |
| D-Galactose |
| Ethanolamine HCl |
| Glutathione (reduced) |
| L-Carnitine HCl |
| Linoleic Acid |
| Linolenic Acid |
| Progesterone |
| Putrescine 2HCl |
| Sodium Selenite |
| T3 (triodo-l-thyronine) |

Composition of N2-supplement

| Components | Concentration (mg/L) |
| --- | --- |
| Proteins | |
| Human Transferrin (Holo) | 10000.0 |
| Insulin Recombinant Full Chain | 500.0 |
| Other Components | |
| Progesterone | 0.63 |
| Putrescine | 1611.0 |
| Selenite | 0.52 |

In preferred embodiments, the neural crest stem cell medium would comprise DMEM (low glucose), 30% neurobasal medium, 15% chick embryo extract, 2% B27 supplement, 1% N2 supplement, 117 nM retinoic acid, 50 µM β-mercaptoethanol, 20 ng/ml insulin-like growth factor (IGF), and 20 ng/ml fibroblast growth factor (FGF). CD34 (+) MeSCs formed larger non-adherent spheroids and these spheroids maintained GFP expression as compared with CD34(−) stem cell populations. For example, neural crest stem cell medium may comprise DMEM-low (Gibco, product 11885-084) and 15% chick embryo extract (prepared as described in Stemple and Anderson, 1992), 20 ng/mL recombinant human bFGF (R&D Systems, Minneapolis, Minn.), 1% N2 supplement (Gibco), 2% B27 supplement (Gibco), 50 M 2-mercaptoethanol, 35 mg/mL (110 nM) retinoic acid (Sigma), penicillin/streptomycin (Biowhittaker), and 20 ng/ml IGF1 (R&D Systems).

Next, the CD34(+) MeSCs and CD34(−) MeSCs from spheroids were subjected to differentiation using neural crest differentiation culture medium containing a similar medium as neural crest stem cell culture. In preferred embodiments, instead of 15% chick embryo extract and 20 ng/ml FGF, the medium contained 1% chick embryo extract and 10 ng/ml FGF. As discussed previously, a person of skill in the art could readily optimize the medium. See, for example "Culturing Nerve Cells," edited by Gary Banker and Kimberly Gosling for proposed culture media.

Once these two cell types from the spheroids differentiated, CD34(+) multipotent neural crest progenitor cells exhibited multiple lineage markers such as myofibroblast, glial, neuronal, K15, and nestin whereas CD34(−) SHG multipotent neural crest progenitor cells did not when in neural crest differentiation medium. In contrast, when these two cell types were introduced into the melanocyte differentiation culture medium, both multipotent neural crest progenitor cell types expressed melanocyte marker (Tyrp1) but only CD34(−) SHG stem cells produced melanized cells. CD34(+) multipotent neural crest progenitor cells expressed higher glial lineage marker indicating these cells possess higher glial lineage potential. Glial cells are known to express Mbp and contribute to the myelination of axons in the CNS and the PNS.

B. Isolated CD34(+) Multipotent Neural Crest Progenitor Cells

MeSCs are cells localized to the bulge/LPP region of the mammalian hair follicle. These MeSCs are identified specifically in this region of the hair follicle by the expression of the proteins Dct and Kit and CD34. Both Dct and Kit are known markers of MeSCs, and CD34 is expressed in the bulge/LPP region of the hair follicle. In certain situations, namely in a Dct-H2BGFP$^{KI}$ mouse which contains both the Dct-tTA$^{KI}$ and the TRE-H2BGFP transgene, these MeSCs express GFP and CD34. As a result, the MeSCs can be separated to provide two subsets based on CD34 expression (i.e., CD34(+) or CD34(−)) and isolated specifically from MeSCs of mouse hair follicles using FACS and other similar techniques.

These techniques include: (i) utilizing the expression of GFP and CD34, (ii) using primary antibodies recognizing CD34 on the cell surface and conjugated to a fluorescent or other suitable optical label, (iii) using secondary antibodies which recognize and bind to a primary antibody binding CD34, and conjugated to a fluorescent or other suitable optical label, (iv) conjugated to another mechanism which enables fluorescent or other suitable optical detection of the CD34-expressing cell. These melanocyte stem cells are further distinguished by their high expression (relative to GFP− or Dct− cells isolated from skin) of the Dct gene and by their high expression (relative to GFP+CD34(−)cells isolated from other regions of the hair follicle) of the Cd34 gene.

CD34+ multipotent neural crest progenitor cells express glial markers and produce a multilayered myelin sheath surrounding unmyelinated neurons. These cells are distinguished from other cells by their recent or distant derivation from a CD34+ MeSC, or its substantial embodiment, as defined above. These CD34(+) multipotent neural crest progenitor cells are located outside of the hair follicle or skin, having been isolated from MeSCs removed from the natural environment by a suitable procedure such as trypsinization or other enzymatic digestion of the skin. The CD34(+) multipotent neural crest progenitor cells are further distinguished by their isolation and separation from CD34(+) MeSCs in the cell suspension of dissociated skin cells using suitable markers, such as expression of GFP in a Dct-H2BGFP$^{KI}$ transgenic background and CD34.

Following the removal of CD34(+) MeSCs from the natural environment and subsequent culture of these CD34(+) MeSCs in neural crest differentiation medium, the resulting CD34(+) multipotent neural crest progenitor cells express Gfap. Furthermore, following removal of CD34(+) MeSCs from their natural environment in skin and co-culturing the CD34(+) MeSCs in neural crest differentiation medium with neurons, the resulting CD34(+) multipotent neural crest progenitor cells express Mbp in a neuronal distribution on proximal neurites and form a myelin sheath surrounding those neurites. These properties are maintained whether the CD34(+) MeSCs are removed from the natural environment and placed thereafter in neuronal co-culture in neural crest differentiation medium, or whether the CD34(+) MeSCs are removed from the natural environment, cultured and expanded for a short or long duration of time, with or without intervening events that can include passaging of the cells, in neural crest stem cell medium, then placed thereafter in neuronal co-culture in neural crest differentiation medium.

Therefore, in one embodiment, the present invention relates to MeSCs comprising CD34(+) multipotent neural crest progenitor cells isolated from hair follicle bulge/LPP of the mammalian hair follicle. The isolated MeSCs may be obtained from any mammal, preferably from a human or a mouse, for example a Dct-H2BGFP mouse.

The isolated population of CD34(+) multipotent neural crest progenitor cells is substantially pure. The isolated cell population of CD34(+) multipotent neural crest progenitor cells includes at least 80% pure, at least 85% pure, at least 90% pure, at least 95% pure, at least 97% pure, at least 98% pure, at least 99% pure, at least 99.5% pure, or at least 99.9% pure CD34(+) multipotent neural crest progenitor cells. These cells may be human or mouse cells (e.g., a Dct-H2BGFP mouse).

In other words, the term "substantially pure" refers to a population of CD34(+) multipotent neural crest progenitor cells that contain fewer than about 0.1%, fewer than about 0.5%, more preferably fewer than about 1%, more preferably fewer than about 2%, more preferably fewer than about 3%, more preferably fewer than about 5%, more preferably than about 10%, more preferably fewer than about 15%, and more preferably fewer than about 20% of other cells, for example, CD34(−) MeSCs. This high level of purity is obtained by following the methods set forth herein (e.g., gene expression, FACS, reanalysis of FACs-isolated cell populations by FACS) without any need for additional purification steps to further purify the cells.

The CD34(+) multipotent neural crest progenitor cells are highly purified after cell sorting, and show a ~400-fold increase in the level of CD34 gene expression compared to CD34(−) MeSCs separated in the same procedure. The data provide evidence that the CD34(+) MeSCs isolated from the skin expressing GFP can be highly purified from other GFP expressing stem cells that do not express CD34. Hence, cells should be greater than 99.5% pure on the basis of CD34 expression. Cells also show a 1000-fold increase in gene expression of the melanocyte stem cell-specific gene Dct compared to non-melanocyte stem cell CD34(+) cells obtained in the same procedure. This result indicates that the CD34(+) MeSCs isolated from the skin also on the basis of GFP expression represent at least a 99.9% pure CD(34+) multipotent neural crest progenitor cell population. Thus, the methods described below provide an efficient, time saving method for producing CD34(+) multipotent neural crest progenitor cells to be used for, but not limited to, therapeutic, research, or other purposes.

In certain embodiments, CD34(+) multipotent neural crest progenitor cells may be described as a mixture of cells at different stages of differentiation towards a mature Schwann cell. See Table 1, Conrad et al., "Embryonic Corneal Schwann Cells Express Some Schwann Cell Markers mRNAs, but No Mature Schwann Cell Marker Proteins" Invest Ophthalmol Vis Sci. 2009 September; 50 (9): 4173-4184.

C. Methods of Producing Dense Myelin Sheaths

Dorsal root ganglion co-culture systems are well established in the art as a model for the study the myelination of neurites. This model system was used to test whether a functional myelin sheath can be produced once a neuron lacks a functional myelin sheath or has become demyelinated. In certain embodiments, a method of producing a dense myelin sheath around an axon. The axon is contacted with the isolated CD34(+) multipotent neural crest progenitor cells under conditions that promote neural crest progenitor formation. These conditions include, but are not limited to, culturing the CD34(+) MeSCs in Poly-D-Lysine and Laminin-coated chambers in the presence of neural crest differentiation medium. Components of the neural crest differentiation medium are available commercially and readily described in the art. In preferred embodiments, neural crest differentiation medium may comprise 10 µM ascorbic acid.

D. Methods of Producing a Functional Myelin Sheath

Demyelination is the loss of the myelin sheath insulating the nerves. It may be immune-mediated, auto-antibody mediated, or caused by a demyelinating disease, trauma, toxin, bacterial infection, viral infection, parasitic infection, or genetic defect. Demyelination is the hallmark of some neurodegenerative autoimmune diseases, including any demyelinating disease or Schwann cell disease described herein, including but not limited to experimental allergic encephalomyelitis, acute disseminated encephalomyopathy, acute hemorrhagic encephalomyelopathy, experimental allergic neuritis, amoebic meningoencephalitis, Guillain-Barré syndrome, multiple sclerosis, stroke, traumatic brain injury, and traumatic peripheral nerve injury, Devic's disease (otherwise known as neuromyelitis optica (NMO), NMO spectrum disorder, progressive multifocal leukoencephalopathy, central pontine myelinolysis, Tabes dorsalis, optic neuritis, transverse myelitis, progressive inflammatory neuropathy, myelopathy, chronic inflammatory demyelinating polyneuropathy, central pontine myelinosis, inherited demyelinating diseases such as leukodystrophy, Charcot-Marie-Tooth disease and visna. Sufferers of pernicious anemia can also suffer nerve damage if the condition is not diagnosed quickly. Subacute combined degeneration of spinal cord secondary to pernicious anemia can lead to slight peripheral nerve damage to severe damage to the central nervous system, affecting speech, balance, and cognitive awareness. When myelin degrades, conduction of signals along the nerve can be impaired or lost, and the nerve eventually withers. A serious myelin deterioration condition is Canavan Disease.

Accordingly, in preferred embodiments, methods are provided for producing a functional myelin sheath on an axon which lacks a functional myelin sheath or has become demyelinated. The axon may be in the central nervous system or peripheral nervous system and is contacted with the isolated CD34(+) multipotent neural crest progenitor cells described herein. Contact may occur by direct injection into the area of the demyelinated neuron or by intrathecal injection, intravenously, or by stereotaxic injection. One of ordinary skill in the art would recognize that the above methods of administration are not limited. Depending on the demyelinating conditions, one may chose an alternative way of administration.

E. Compositions and Kits

Isolated CD34(+) multipotent neural crest progenitor cells described herein can be formulated into compositions, in particular therapeutic compositions. Accordingly, compositions comprising CD34(+) multipotent neural crest progenitor cells are described herein.

The ability to preserve stem cells is critical for their use in clinical and research applications. Preservation of cells permits the transportation of cells between sites, as well as completion of safety and quality control testing. Preservation permits development of cell banks with different major histocompatibility complex genotypes and genetically modified clones. As collection of stem cells from sources such as umbilical cord blood can be difficult to predict or control, the ability to preserve cells permits the banking of stem cells until later use in the research lab or clinical application. The ability to preserve cells permits completion of quality and safety testing before use as well as transportation of the cells between the sites of collection, processing and clinical administration. Finally, the ability to preserve cells used therapeutically facilitates the development of a manufacturing paradigm for stem cell based therapies.

Losses during transfer and dilution can be minimized by using an "acceptable carrier", such as specific "stabilizing agents" including but not limited to heparin, platelet-derived growth factors (Yeh et al., 1993) and stem cell factors. In certain embodiments, these compositions can include CD34 (+) multipotent neural crest progenitor cells that are in acceptable carriers that are compatible with the CD34(+) multipotent neural crest progenitor cells. Optionally, the compositions also may contain other ingredients, such as hormones or other factors which can assist in appropriate differentiation of the cells to be administered.

In certain embodiments, a composition may be administered in a number of ways either alone or in combination with other treatments, either simultaneously or sequentially depending on the condition to be treated and whether local or systemic treatment is desired. Administration may be by direct injection into the area of demyelination, or by intrathecal injection, or intravenously, or by stereotaxic injection. The route of administration can be selected based on the disease or condition, the effect desired, and the nature of the cells being used. Actual methods of preparing dosage forms are known, or will be apparent, to those skilled in the art. (See Remington's Pharmaceutical Sciences, 20$^{th}$ Edition, 2000, pub. Lippincott, Williams & Wilkins.) Where a composition as described herein is to be administered to an individual, administration is preferably in a "prophylactically effective amount" or a "therapeutically effective amount," this being sufficient to show benefit to the individual.

The number of administrations can vary. Introducing CD(34+) multipotent neural crest progenitor cells in the subject can be a one-time event. Alternatively, administration may be, for example, daily, weekly, or monthly. The actual amount administered, and rate and time-course of administration, will depend on the age, sex, weight, of the subject, the stage of the disease, and severity of what is being treated. Prescription of treatment, e.g., decisions on dosage is within the responsibility of general practitioners and other medical doctors.

The materials described herein as well as other materials can be packaged together in any suitable combination as a kit useful for performing, or aiding in the performance of, the disclosed method. It is useful if the kit components in a given kit are designed and adapted for use together in the disclosed method. For example disclosed are kits for isolating CD34(+) MeSCs from skin cells, the kit including antibodies specific for detection and sorting of cells expressing CD34(+). The kits also can contain media for proliferating, storing, differentiating, and/or inducing the cells. The kits can also contain materials for collection of cells.

Compositions may be placed within containers, or kits, along with packaging material which provides instructions regarding the use of such pharmaceutical compositions. Generally, such instructions will include a tangible expression describing the reagent concentration, as well as within certain embodiments, relative amounts of excipient ingredients or diluents (e.g., water, saline or PBS) which may be necessary to reconstitute the pharmaceutical composition.

5. SUMMARY OF EXPERIMENTAL RESULTS

The following is a summary of results of experiments described in the Examples of this application:

Dct-H2BGFP$^{ki}$ bitransgenic mice have nuclear GFP-expressing melanocyte precursors in the bulge/LPP (CD34(+)) and SHG (P-cad+) of telogen HFs of dorsal skin and tail and were separated based on CD34 expression;

CD34-GFP+ (SHG) melanocyte precursors express higher levels of melanogenic genes and produced higher percentage of pigmented cells when grown in melanocyte differentiation medium;

CD34(+)GFP+ (bulge/LPP) MeSCs form larger spheroids under neural crest stem cell differentiation conditions and also express multiple neural crest cell lineage markers when induced to differentiate in neural crest cell differentiation medium;

In DRG co-culture system, differentiated CD34(+)GFP+ (bulge/LPP) multipotent neural crest progenitor cells express myelin basic protein and contribute to myelination of surrounding axons; and These findings showed that bulge/LPP CD34(+) MeSCs are capable of neural crest lineage differentiation to produce cells that can functionally myelinate neurons.

6. EXAMPLES

The invention is illustrated herein by the experiments described by the following examples, which should not be construed as limiting. The contents of all references, pending patent applications and published patents, cited throughout this application are hereby expressly incorporated by reference. Those skilled in the art will understand that this invention may be embodied in many different forms and should not be construed as limited to the embodiments set forth herein. Rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

Example 1

Materials and Methods

Generation and Characterization of Dct-H2BGFP$^{KI}$ Bitransgenic Mouse Model.

A knock-in mouse model expressing the tetracycline-regulated transactivator (tTA) gene under the control of the murine dopachrome tautomerase (Dct) melanocyte specific promoter was used to identify MeSCs. The transgenic mouse was generated to allow a melanocyte specific tTA transactivation in vivo. The transgenic cassette expressing the tTA gene under the control of the Dct promoter was inserted in the Hprt gene. The Hprt gene is localized on the X-chromosome. This transgenic mouse was then crossed with TRE-H2BGFP mice to generate a bitransgenic mouse model. The Dct-tTA knock-in mouse was designed to drive expression of H2BGFP constitutively in bitransgenic Dct-tTA knock-in;TRE-H2BGFP mice in the absence of doxycycline. See FIG. 6A-6E for photographs providing a characterization of the Dct-TtaKIH2b-Gfp bitransgenic mouse model.

Immunofluorescence Assay

Figure 11A:
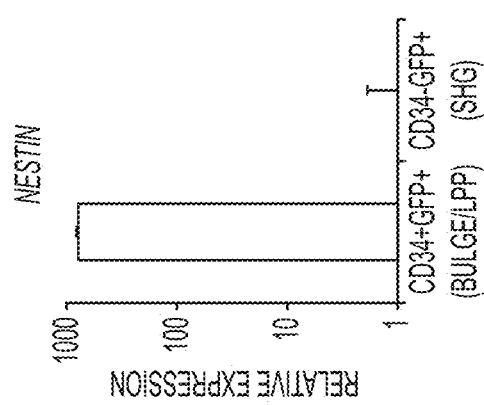
FIG. 11A-11B demonstrate that CD34(+) bulge/LPP melanocyte stem cells exhibit the neuronal stem cell marker nestin with a comparison of expression of nestin RNA (FIG. 11A) and nestin protein (FIG. 11B) in CD34(+) bulge/LPP versus CD34(−) SHG melanocyte stem cells.
Figure 11B:
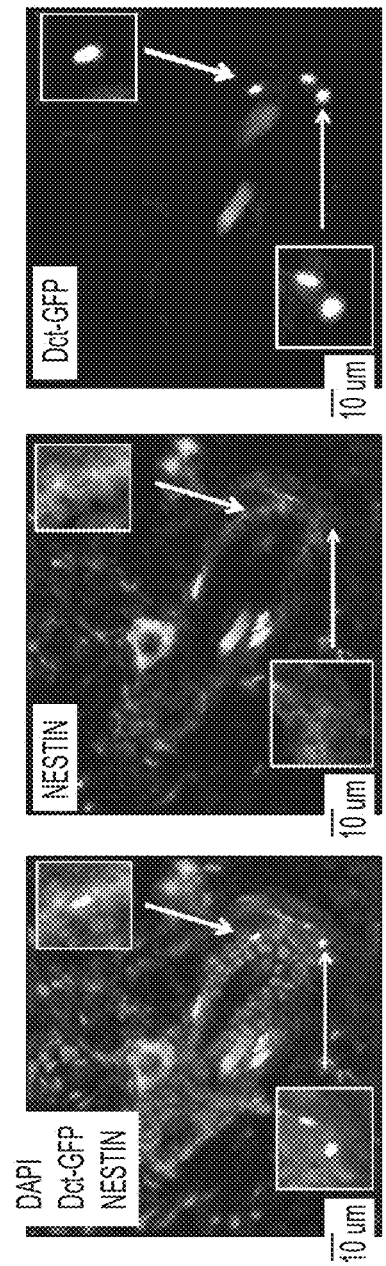

Dorsal skin obtained from the transgenic mice at the indicated ages was embedded in OCT compound and cryosections cut with a thickness of 10 μm to observe H2BGFP expression. For immunofluorescence, cryosections were fixed in 4% paraformaldehyde in PBS for 10 min at room temperature and blocked with blocking buffer (10% FBS, 1% BSA and 0.1% Triton-x) for 1 hour at room temperature. Primary antibodies for CD34 (rat monoclonal antibody, clone Ram34, BD Biosciences), P-Cadherin (goat polyclonal antibody, R & D Systems), c-Kit (rat monoclonal antibody, Cedarlane), Dct (alpha-Pep-8) (rabbit polyclonal antibody, a gift from Dr. Vincent Hearing, NIH), or nestin (mouse monoclonal antibody, Chemicon) at 1:200 dilution were added and incubated at 4° C. overnight. To detect the primary antibody, isotype-matched Cy3-conjugated secondary antibodies (Jackson Immunogenetics) or Alexa 647-conjugated secondary antibodies (Invitrogen) were added at a 1:1000 dilution and incubated for 1 hour at room temperature. Coverslips were mounted using mounting solution with DAPI (Vectashield, Vector Laboratories). Fluorescence was detected using an Olympus upright fluorescence microscope, Slidebook imaging software. See FIG. 11A-11B also, for data demonstrating that CD34(+) bulge/LPP melanocyte stem cells exhibit the neuronal stem cell marker nestin with a comparison of expression of nestin RNA (FIG. 11A) and nestin protein (FIG.11B) in CD34(+) bulge/LPP versus CD34(−) SHG melanocyte stem cells.

For immunofluorescence detection in primary-cultured cells, cells were washed with PBS and fixed with 4% PFA at room temperature for 10 min. PBS containing 10% FBS and 1% BSA was used for blocking at room temperature for 1 hour. After blocking, cells were incubated with 1:200 dilution of primary antibodies for α-SMA (mouse monoclonal antibody, Sigma Aldrich), GFAP (rabbit polyclonal antibody, Dako), Tuj1 (mouse monoclonal antibody, Sigma Aldrich), K15 (mouse monoclonal antibody, Chemicon), Tyrp1 (alpha-Pep-1) (rabbit polyclonal antibody, a gift from Dr. Vincent Hearing, NIH), β-Actin, or Mbp (rat monoclonal antibody, Abcam) at 4° C. overnight followed by incubation with Cy3-conjugated secondary antibody or Alexa 647-conjugated secondary antibody at room temperature for 1 hour. Coverslips were mounted using mounting solution with DAPI (Vectashield, Vector Laboratories). Fluorescence was detected using an Olympus upright fluorescence microscope, Slidebook imaging software.

Figure 7A:
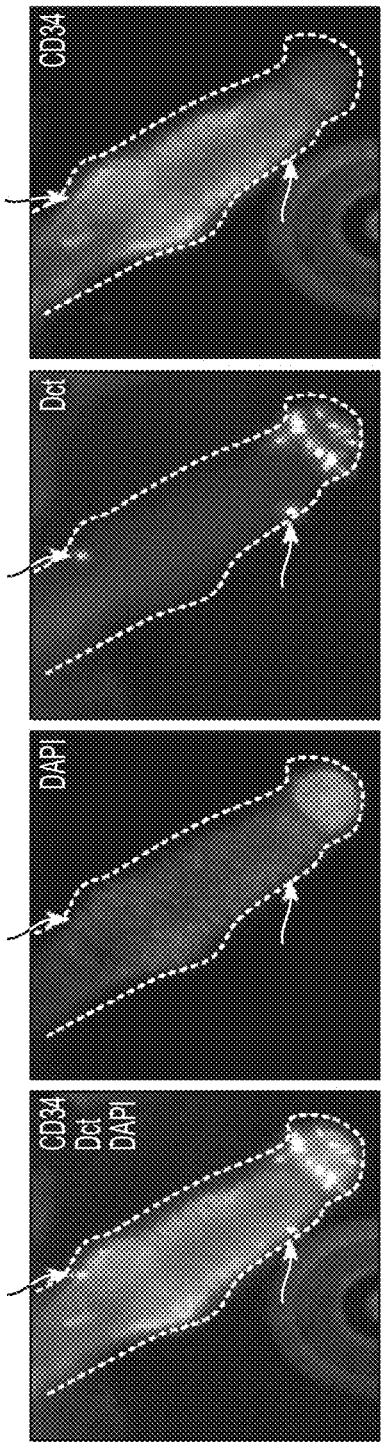
FIG. 7A-7B are photographs showing GFP-expressing melanocyte precursors in whole mount telogen hair follicles. The photographs show P56 whole mount hair follicles of mouse tail epidermis, demonstrating GFP expression in CD34(+) bulge/LPP cells (FIG. 7A, arrowheads) and P-cad+ SHG cells (FIG. 7B, arrowheads).
Figure 7B:
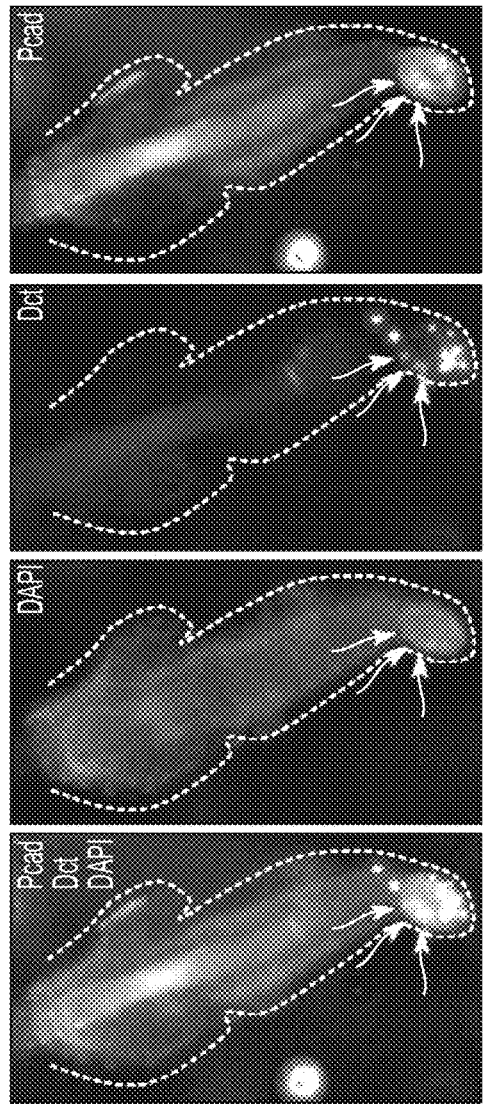
Figures 8A, 8B:
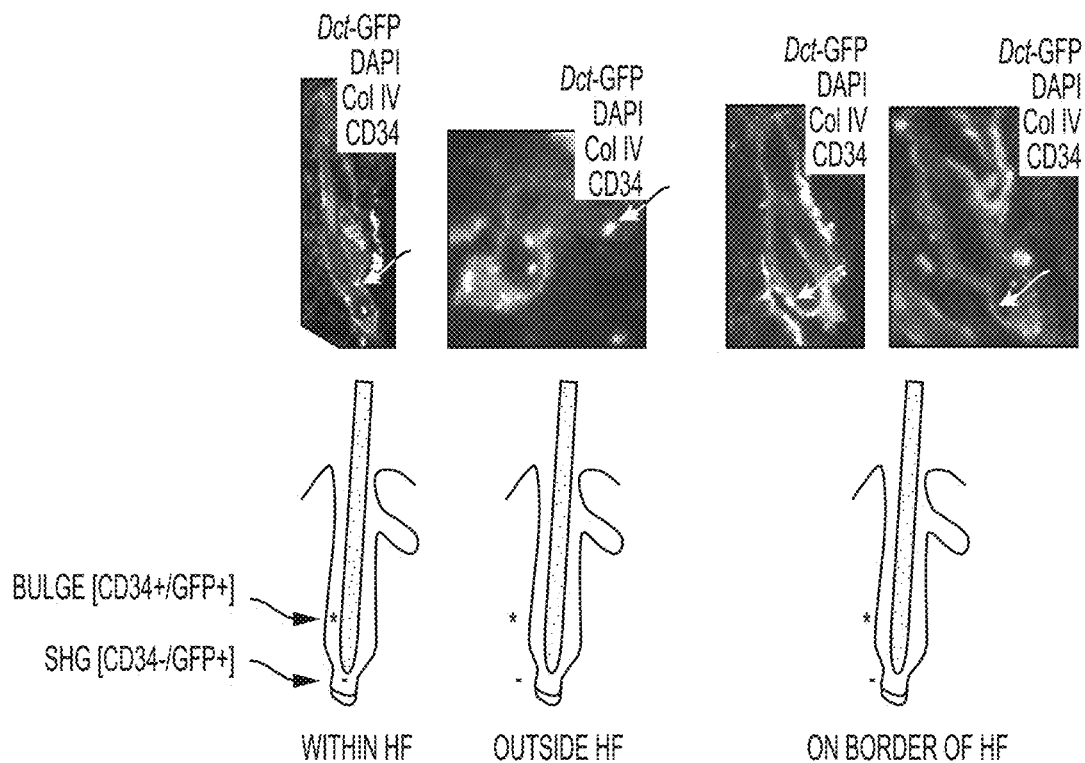
FIG. 8A-8B show quantitation of GFP-expressing cells within and outside of the hair follicles.

For whole mount hair follicle staining, whole mounts of mouse tail epidermis were prepared as described previously (Bruan et al., 2003 and Estrach S et al., 2006). A scalpel was used to slit the tail lengthways. Skin was peeled from the tail, cut into pieces (0.5×0.5 cm$^2$) and incubated in 5 mM EDTA in PBS at 37° C. for four hours. Forceps were used to gently peel the intact sheet of epidermis away from the dermis and the epidermal tissue was fixed in 4% formal saline (Sigma) for 2 hours at room temperature. Fixed epidermal sheets were stored in PBS containing 0.2% sodium azide at 4° C. for up to 8 weeks prior to labelling. For immunofluorescence staining of whole mount hair follicle, epidermal sheets were blocked and permeabilised by incubation in blocking buffer containing 10% FBS, 1% BSA and 0.5% Triton-X in PBS for 30 minutes. Primary antibodies were diluted in the blocking buffer and tissue was incubated overnight at 4° C. with gentle agitation. Epidermal whole mounts were then washed for at least 4 hours in PBS, changing the buffer several times. Incubation with secondary antibodies was performed in the same way. Samples were rinsed in distilled water and mounted in mounting solution with DAPI. See FIG. 7A-7B for photographs showing GFP-expressing melanocyte precursors in whole mount telogen hair follicles. See also FIG. 8A-8B, showing quantitation of GFP-expressing cells in locations of the hair follicle.

Preparation of Single Cells from Dermal Skin and Fluorescence Activated Sorting (FACS)

Dorsal skin samples were obtained from transgenic mice at different ages immediately following euthanasia and fat was removed from the dermis using fine forceps. Defatted skin was incubated in 0.5% of trypsin (USB) dissolved in PBS at 37° C. for 30 min. Epidermis was peeled away from the dermis following incubation, and the remaining dermis was cut into small pieces. The cut dermal pieces are placed in to digestion medium containing 0.2 mg/ml Liberase Thermolysin low (Roche) and were incubated in 37° C. water bath for 45 to 60 min. The digested dermal mixture was added into PBS containing 0.05% DNase (Sigma) and 5% FBS. Single cells could be extracted from the dermis by repeated plunging with a 60 cc syringe followed by filtration through 40 μm nylon mesh (BD Falcon). The dermal cell suspension was generated in 5% FBS/PBS and was ready to stain with respective antibodies and FACS. This procedure was done under aseptic conditions.

Figure 9A:
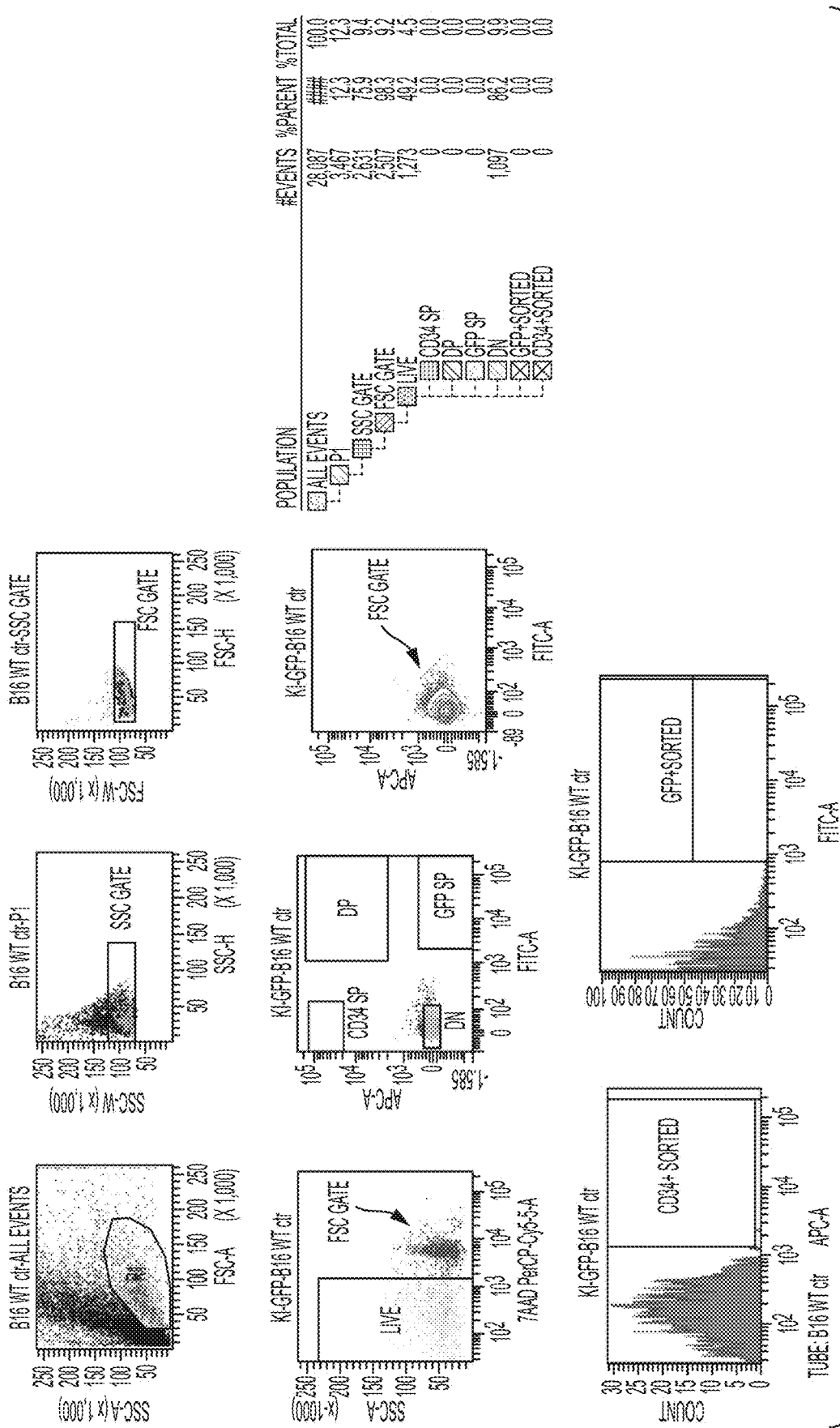
FIG. 9A-9B show representative FACS sorting schemes used for isolation of bulge/LPP and SHG melanocyte precursors, based on GFP and CD34 markers from wild type (FIG. 9A) and Dct-TtaKIH2b-Gfp mouse (FIG. 9B) skin hair follicles.
Figure 9B:
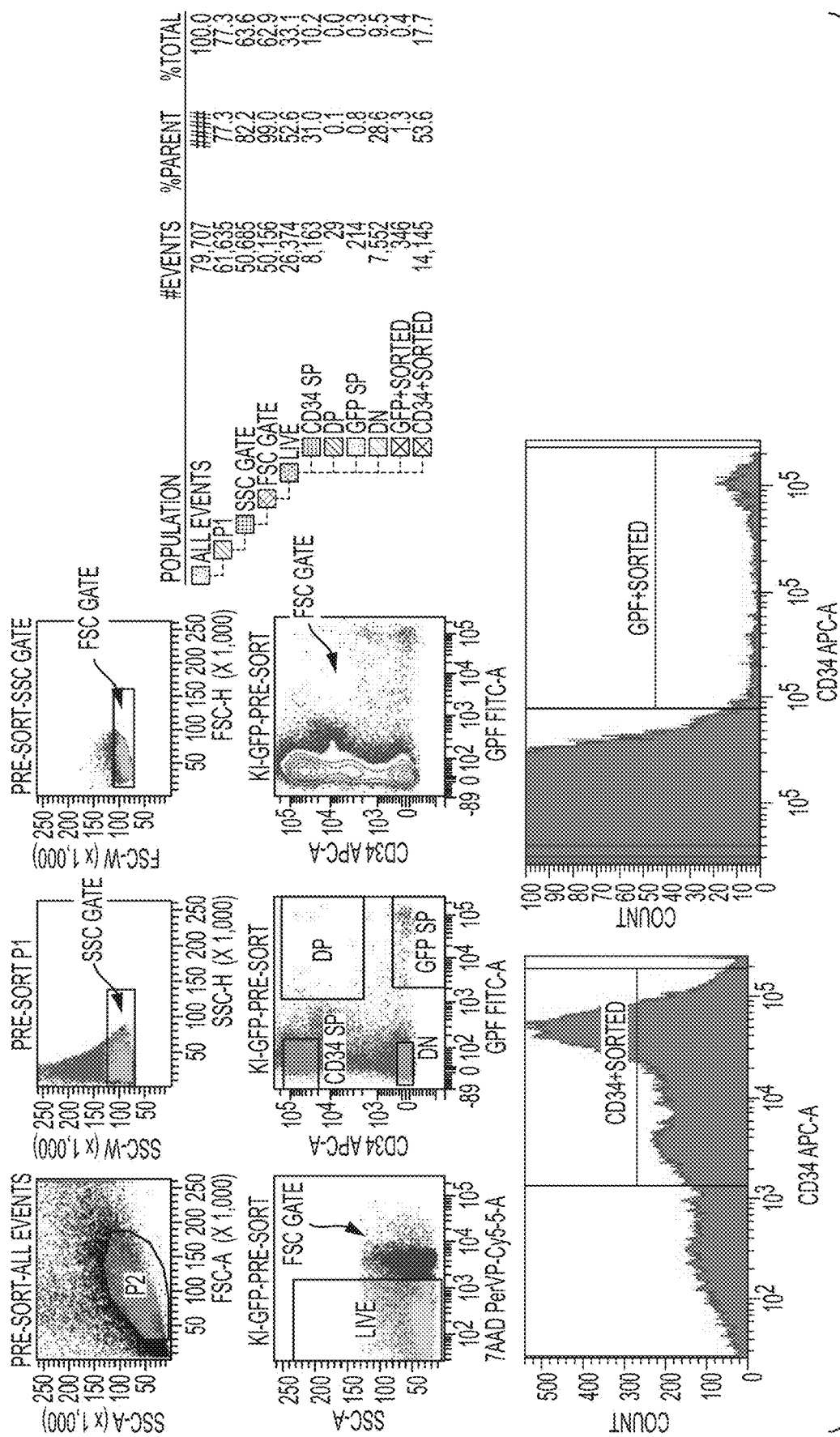
Figure 13A:
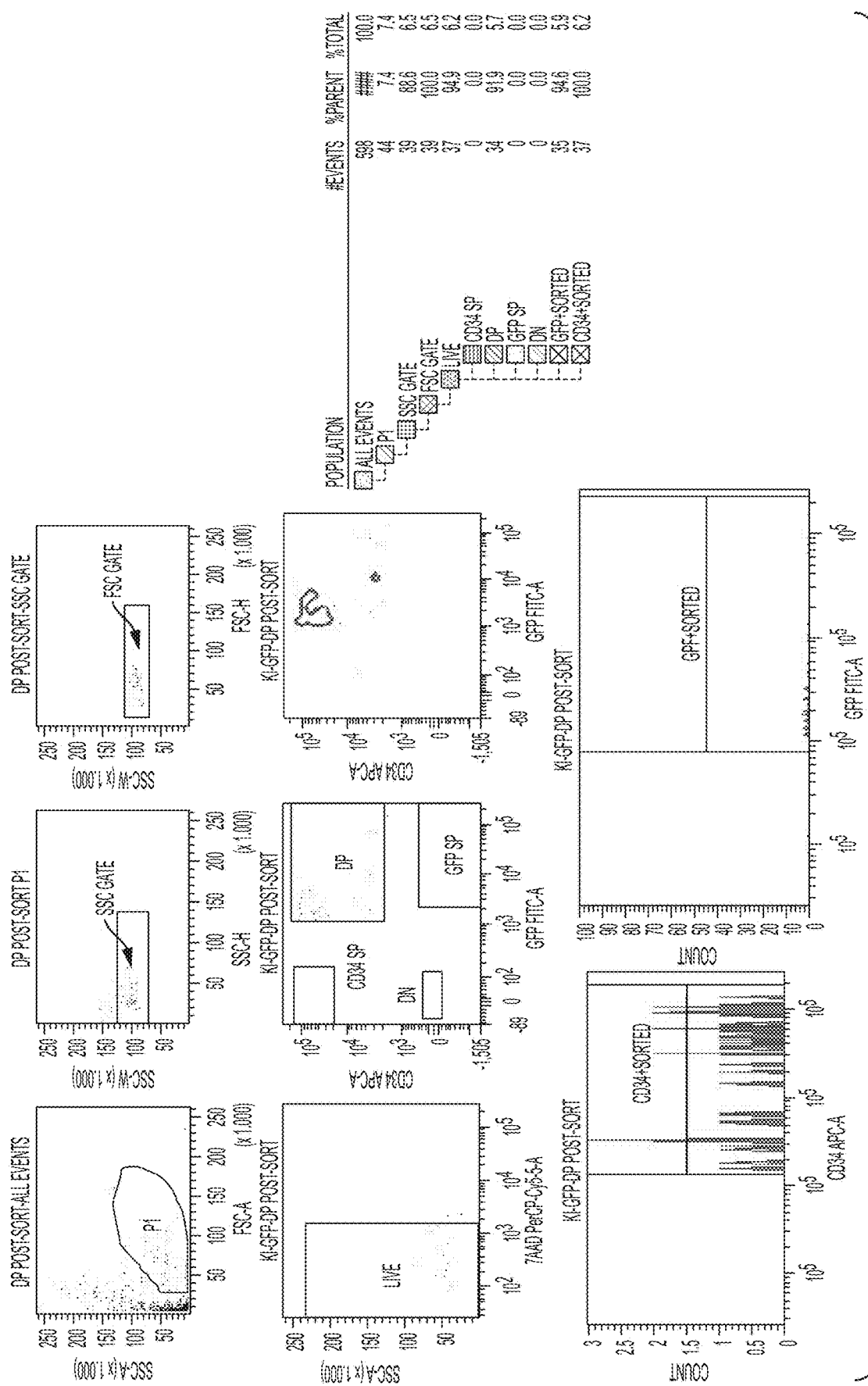
FIG. 13A-13B show a reanalysis for the purity of CD34 (+)GFP(+) bulge/LPP cells (FIG. 13A) and CD34(−)GFP(+) SHG cells (FIG. 13B) FACS-sorted melanocyte precursors. A few hundred cells were reanalyzed from each sorted population to test the effectiveness of the sorting methods.
Figure 13B:
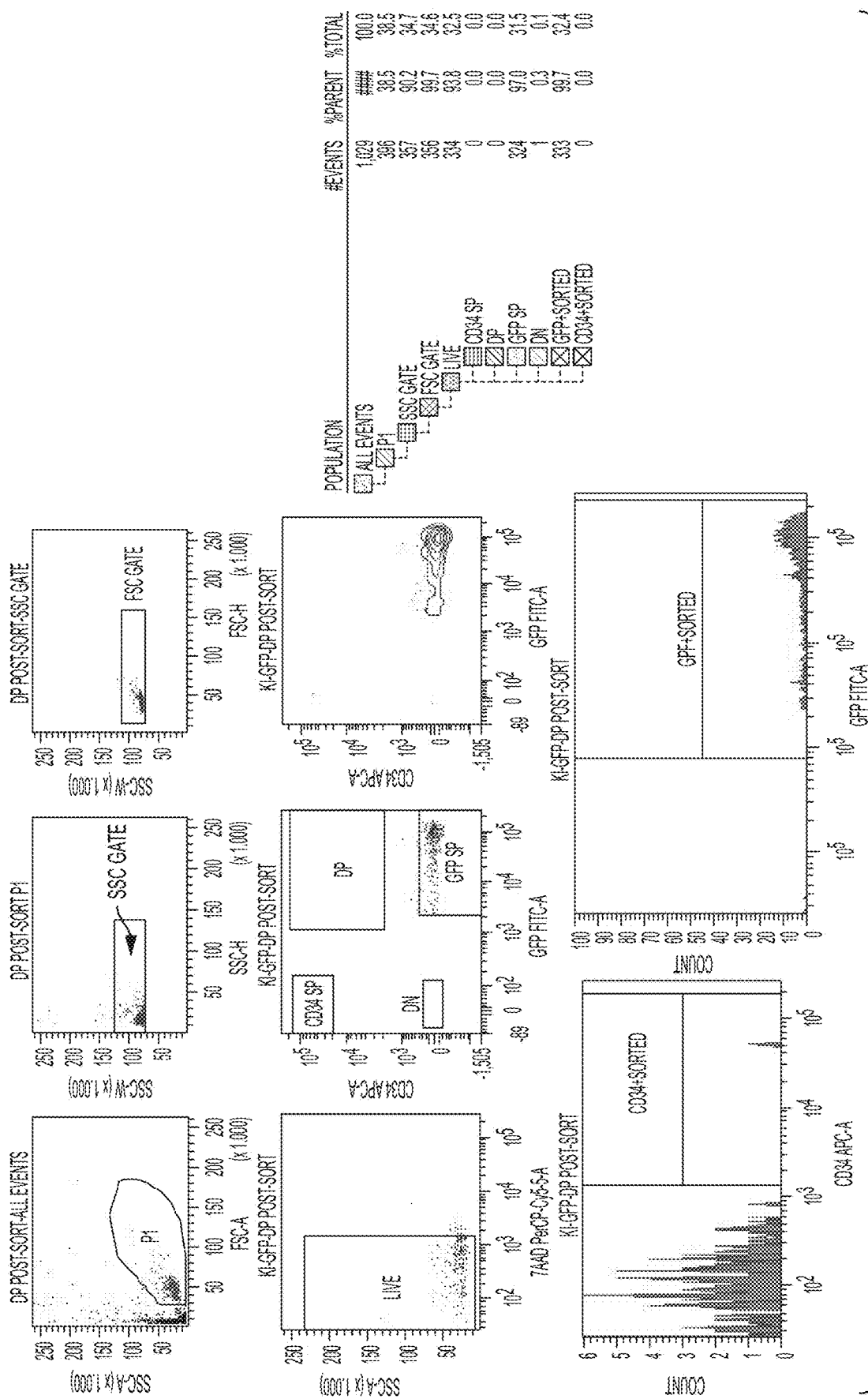

To separate the hair follicle bulge/LPP and SHG cells of Dct-H2BGFP$^{ki}$ bitransgenic mice FACS with GFP and anti-CD34 marker the dermal cells were incubated with Alexa 647-conjugated anti-CD34 antibody in for 30 min at 4° C. 7-AAD was added to the CD34 labeled dermal cell suspension in 5% FBS/PBS, and cell sorting was performed using a BD FACSAria1 instrument (Becton-Dickenson). Sorted cells were counted and used either for primary cultures or for quantitative real-time PCR (qRT-PCR) by extracting RNA from respective cell populations. See FIG. 9A-9B for representative FACS sorting schemes. See also FIG. 13A-13B, which provide FACS reanalysis for the purity of CD34(+) GFP(+) bulge/LPP cells (FIG. 13A) and CD34(−)GFP(+) SHG cells (FIG. 13B) FACS-sorted melanocyte precursors. A few hundred cells were reanalyzed from each sorted population to test the effectiveness of the sorting methods.

RNA Extraction, cDNA Synthesis and qRT-PCR

Figure 10:
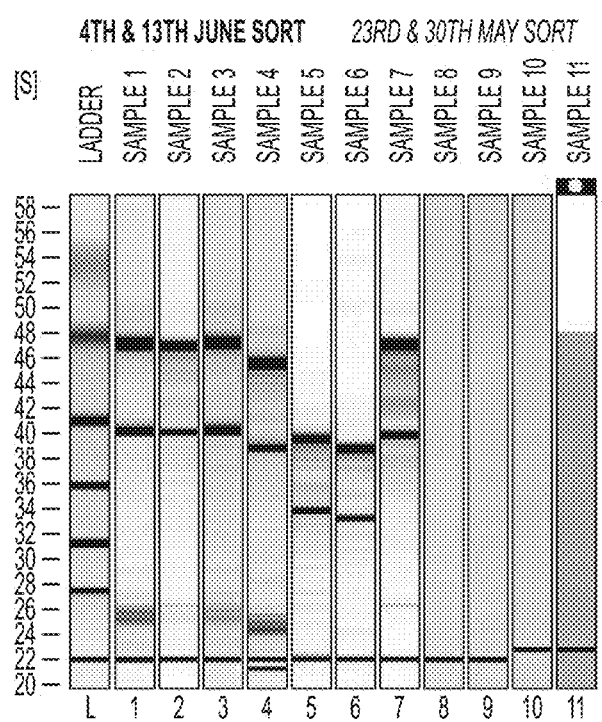
FIG. 10 shows analysis of the total RNA extracted from the FACS-sorted GFP(+) melanocytes.

Total RNA was extracted from sorted cells using RNeasy Micro Kit (Qiagen) as per manufacturer's protocol. The cell lysate in RNA solution was mixed with equal volume of 70% ethanol and transferred to a spin column. After series of centrifugation, incubation with a DNase I incubation mix and washing with washing solution, the spin column membrane was eluted with 14 µl RNase free water. The quantity and quality of isolated RNA was determined with an Agilent 2100 Bioanalyzer using RNA PicoChips (Agilent). To synthesize first-strand cDNA from total RNA the SuperScript III First-Strand Synthesis System for RT-PCR (Invitrogen) was used. The total RNA was incubated with random hexamer primer along with dNTP at 65° C. for 5 min, added to a mixture of reverse transcriptase, MgC12, RNaseOUT, DTT and reaction buffer incubated at 25° C. for 10 min, followed by 50° C. for 50 min and reaction is terminated at 85° C. for 5 min incubation. qRT-PCR analysis for the differential gene expression among the sorted cell population was determined using LightCycler 480 SYBER Green I Master (Roche) and running them on LightCycler 480 instrument (Roche). See FIG. 10 for analysis of the total RNA extracted from the FACS-sorted GFP(+) melanocytes.

In Vitro Cell Culture

To study the melanocyte differentiation potential of bulge/LPP and SHG MPCs from telogen HFs, these cell types were introduced into a melanocyte differentiation condition. For melanocyte differentiation culture, cells were plated in 24 well plates with melanocyte differentiation inducing culture medium containing 5% FBS, stem cell factor (SCF) (50 ng/ml; Peprotech), endothelin-3 (20 nM; Sigma), basic fibroblast growth factor (FGF) (2.5 ng/ml; R&D Systems), α-melanocyte stimulating hormone (α-MSH) (100 nM; Sigma), phosphoethanolamine (1 µM; Sigma), ethanolamine (10 µM; Sigma), insulin (1 mg/ml; Sigma) and 1% Penicillin/streptomycin in RPMI 1640 medium.

For spheroid formation, cells were cultured in ultra-low attachment 24 well plates, with neural crest stem cell medium as described previously (Bixby S et al., 2002 and Pfaltzgraff E R et al., 2012) containing DMEM (low glucose), 30% neurobasal Medium, 15% chick embryo extract, 2% B27 supplement, 1% N2 supplement, 117 nM retinoic Acid, 50 µM β-mercaptoethanol, 20 ng/ml insulin-like growth factor (IGF), 20 ng/ml FGF and 1% penicillin/streptomycin. For neural crest multi-lineage cell culture study, cells were cultured in 30 µg/ml fibronectin coated 8-well chamber slides in neural crest differentiation culture medium containing similar medium (with 1% chick embryo extract and 10 ng/ml FGF) for 8 days as described previously (Bixby S. et al., 2002).

Rat glial precursor cells (Invitrogen) were cultured on Poly-D-Lysine coated plates in glial precursor cell growth medium containing Knockout DMEM/F-12, 2 mM Glutamax supplement, 2% StemPro NSC SFM supplement, 20 ng/ml FGF, 20 ng/ml EGF, and 10 ng/ml PDGF-AA as per the manufacturer's descriptions. To induce differentiation of glial precursor cells into mature oligodendroglial cells (ODC), cells were cultured on Laminin and Poly-D-Lysine coated plates in glial differentiation culture medium containing similar medium (without PDGF-AA and FGF).

Dorsal Root Ganglion (DRG) Co-Cultures

Isolation and culture of DRGs from Shiverer pups was performed as described previously (O'Meara R W et al., 2011). Shiverer pups (P5 to P8) were euthanized according to institutional guidelines and the spine is extracted. The excess muscle and bone from the spine was trimmed away and placed in a petri dish with a ventral side-up. Using dissection scissors, the spinal column was cut medially starting caudally in a longitudinal fashion. The spinal column was gently opened by two pairs of forceps and the spinal cord was exposed. DRGs were found beneath and lateral to the spinal cord. Using fine tipped forceps the DRGs were removed and transferred to ice cold Hank's buffered salt solution in a new Petri dish. DRGs were transferred to a 1.5 mL centrifuge tube containing 500 µL of ice cold HBSS and were pelleted by spinning at 1200 rpm for 5 min at 4° C. Supernatant is discarded and a 500 µL of pre-warmed DRG papain solution is added and DRGs are incubated at 37° C. for 10 min. Supernatant was discarded and a 500 µL of pre-warmed Collagenase A solution was added and DRGs were incubated at 37° C. for 10 min. Supernatant was discarded and DRGs were washed twice with 1 mL of DRGN media (DMEM containing 10% FBS). Finally, DRGs were dissociated by triturating them with the BSA-coated glass pasture pipette and once dissociation is achieved, the suspension was passed through a 40 µm filter into a sterile Petri dish containing 7 mL of DRGN media. The Petri dish was incubated at 8.5% $CO_2$ for 1 hour 15 min. During this step many contaminating cells including fibroblast and glial cells strongly adhered to the Petri dish, thereby enriching cell suspension for DRGs. The cell suspension containing DRGs was collected by pelleting and was cultured in 10 ug/ml laminin and 30 ug/ml Poly-D-Lysine coated 24 well plate in DRGN media in 37° C. tissue culture incubator at 8.5% $CO_2$ overnight. The next day, DRGN media was replaced with OL media (DMEM with 2% B27 supplement, 1% N2 Supplement, lx glutamine, 0.5% FBS and 1% penicillin/streptomycin) and with a 10 µM 5'-Fluro-deoxyuridine (FuDR) to prevent the proliferation of contaminating fibroblasts and glial cells. On Day 5, full media was changed with OL media (without FuDR) and on Day 7 the DRGs formed an extensive neurite bed, ready to be co-cultured.

Figure 12B:
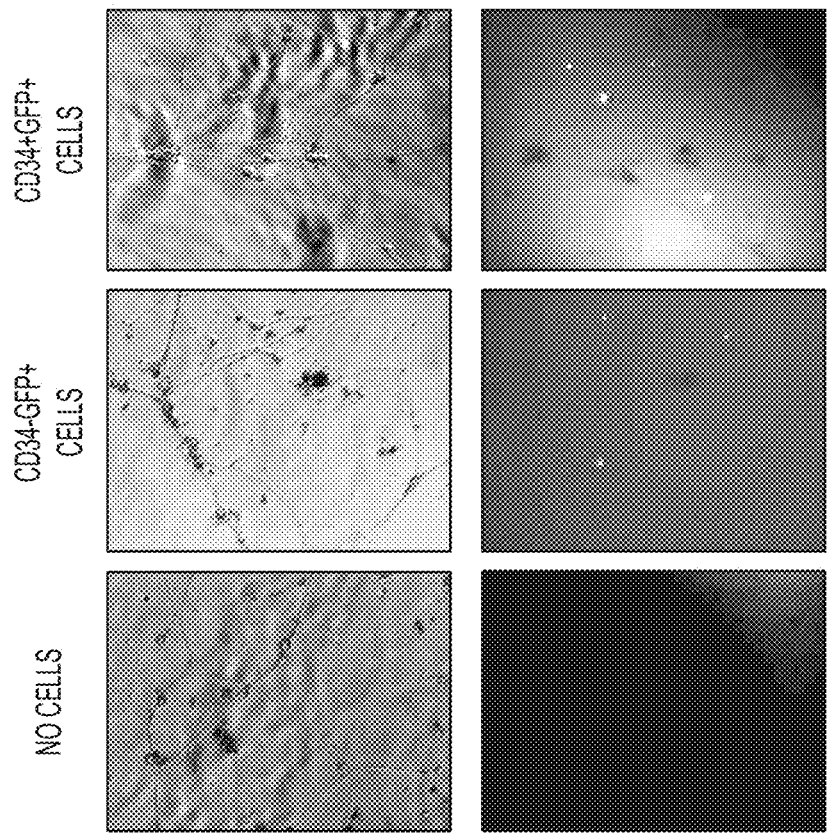
FIG. 12A-12B relate to co-cultures of cells according to an embodiment of the invention and Shiverer dorsal root ganglia.
Figure 12A:
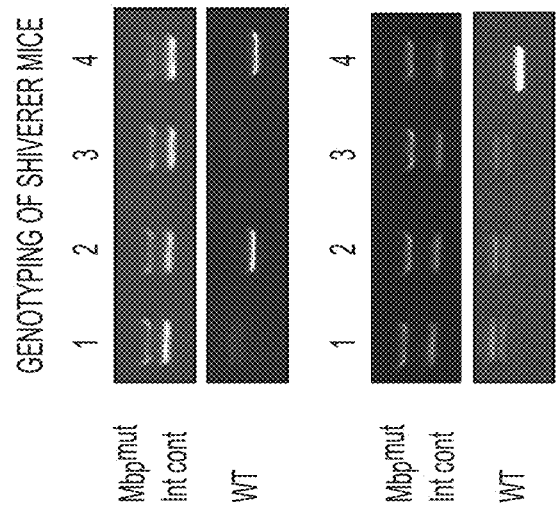

For DRG co-cultures, CD34(+) or CD34(−)MeSCs isolated from Dct-Tta$^{KT}$H2b-Gfp mouse skin or rat oligodendroglial cells (ODC) (Invitrogen) were then seeded onto the dense neuronal bed generated either by Shiverer or rat embryonic DRGs. For co-cultures of CD34(+) or CD34(−) MeSCs, Shiverer or rat embryonic DRGs, cells were cultured in Poly-D-Lysine and Laminin-coated neural crest differentiation medium containing 10 µM ascorbic acid to induce myelination. For co-cultures of rat ODCs and Shiverer DRGs, cells were cultured in glial cell differentiation medium. After one week of co-culture, cells were fixed and subjected to study myelination of axons by immunostaining for the expression of Mbp and myelin sheath formation by electron microscopy. See FIG. 12A-12B for data relating to co-cultures of cells according to an embodiment of the invention and Shiverer dorsal root ganglia, including Shiverer mouse genotyping and photomicrographs of the co-cultures.

Electron Microscopy

The preparation of DRG co-cultures for electron microscopy was achieved by removing the medium and washing twice with the sodium cacodylate buffer (0.1M sodium cacodylate+3 mM CaCl2; PH 7.4). The DRG cells from co-cultures were fixed with 3% glutaraldehyde in sodium cacodylate buffer for 30 min at room temperature and then cool at 4° C. They were then postfixed in 1% osmium ferricyanide and 2% uranyl acetate, dehydrated in ascending ethanol concentrations, rinsed in acetonitrile, and embedded in Spurr's epoxy resin. Following sectioning, they were stained with saturated uranyl acetate in 50% ethanol and lead citrate, and viewed in a Philips/FEI BioTwin CM120 transmission electron microscope operated at 80 kV.

Statistical Analysis

The statistical analysis for the qRT-PCR of differential gene expression among sorted cells (FIG. 2C FIG. 3A) was performed using one-way ANOVA. For the quantification data of the bulge/LPP and SHG melanocyte precursor cell potential to produce pigmented melanocytes in melanocyte differentiation medium at $4^{th}$ and $7^{th}$ day (FIG. 3C), two-way ANOVA was applied, n=5 independent determinations for bulge/LPP and SHG melanocyte precursor cell images. The statistical analysis for the quantification of bulge/LPP MeSCs and SHG melanocyte precursor cells ability to form larger spheroids when cultured in neural crest stem cell medium measured at $2^{nd}$, $4^{th}$, $6^{th}$ and $8^{th}$ day (FIG. 4B) was determined using two-way ANOVA, n=5 independent determinations for bulge/LPP and SHG melanocyte precursor cell images.

List of Primer Sequences

Mouse Dct

Forward: 5' TTCGCAAAGGCTATGCGC-3' (SEQ ID NO: 1)
Reverse: 5' GTTACTACCCAGGTCAGGCCAG-3'. (SEQ ID NO: 2)

Mouse Cytokeratin 14

Forward: ATCGAGGACCTGAAGAGCAA (SEQ ID NO: 3)
Reverse: GGCTCTCAATCTGCATCTCC (SEQ ID NO: 4)

Tyr

Forward: 5' CGGCCAACGATCCCATT-3' (SEQ ID NO: 19)
Reverse: 5' TGCCTTCGCAGCCATTG-3' (SEQ ID NO: 5)

TyrP1

Forward: 5' GTGTTCCCTAGCTCAGTTCTCTGG-3' (SEQ ID NO: 6)
Reverse: 5' TCCTCTGACTGATACCTT-3' (SEQ ID NO: 7)

Gapdh

Forward-TGCAGTGGCAAAGTGGAGATTGTTG (SEQ ID NO: 20)
Reverse-TGTAGCCCAAGATGCCCTTCAG. (SEQ ID NO: 8)

Pmel17

Forward: 5'-TCCAGGAATCAGGACTGGCTTGGT-3' (SEQ ID NO: 9)
Reverse: 5'-GTGAAGGTTGAACTGGCGTG- 3' (SEQ ID NO: 10)

P-Cad

FWD 5'-ACAGCATCACAGGGCCTGGC-3' (SEQ ID NO: 11)
REV 5'-TGGCTCCTTCGGCTCTTGGC-3' (SEQ ID NO: 12)

Shiverer Genotyping
Mutant primer (303 bp)

$Mbp^{shi}$ Fwd
ACC GTC CTG AGA CCA TTG TC (SEQ ID NO: 13)

$Mbp^{shi}$ Rev
GTG CTT ATC TAG TGT ATG CCT GTG (SEQ ID NO: 14)

Internal positive control (200 bp)

Control Fwd
CAA ATG TTG CTT GTC TGG TG (SEQ ID NO: 15)

Control Rev
GTC AGT CGA GTG CAC AGT TT (SEQ ID NO: 16)

WT shiverer primer (411 bp) {overlaps $3^{rd}$ exon and $3^{rd}$ intron}

$WT^{shi}$ Fwd
GGCCGGACCCAAGATGAAAAC (SEQ ID NO: 17)

$WT^{shi}$ Rev
TGTTGGCCTAAAGCACCCTAC (SEQ lD NO: 18)

Example 2

Identification of GFP-Expressing MPCs in Bulge/LPP and SHG of Telogen HF

To identify melanocyte label-retaining cells with the properties of melanocyte stem cells (MeSCs) in the telogen, or resting stage, murine hair follicle (HF), Dct-H2BGFP mice were developed. Dct-H2BGFP mice are bitransgenic mice with both the Dct-tTA and TRE-H2BGFP transgenes. To overcome problems with the fidelity of expression of randomly inserted Dct-tTA transgenes, instead a version of Dct-tTA mice was generated in which the transgene was inserted into the Hprt gene locus using gene targeting. By manipulating the administration of doxycycline to these mice, quiescent melanocyte label-retaining cells (LRCs) could be generated and visualized in the telogen HF. Similar to cells from the Tet-On iDct-GFP mice, Dct-H2BGFP cells were present in both the CD34-expressing bulge/LPP region of the HF and the CD34-negative, P-cadherin-expressing secondary hair germ (SHG) region at the base of the telogen HF (FIG. 1A and FIG. 1B). Dct-H2BGFP cells in second telogen expressed the MeSC markers Kit (FIG. 1C) and Dct (FIG. 1D). Careful observation of Dct-H2BGFP cells in the bulge/LPP HF region revealed not only that these cells were present in the CD34(+) region, but also appeared to express CD34 (FIG. 1E).

Example 3

Isolation and Characterization of CD34(+) vs. CD34(−)MeSCs in HF at $2^{nd}$ Telogen CD34 expression selectively by bulge/LPP Dct-H2BGFP cells provided a strategy to separate these cells from SHG Dct-H2BGFP cells to evaluate their molecular and functional properties. Single cell suspensions prepared from shaven, dorsal skin of approximately 8-week-old (P56) mice, an age when all HFs are synchronously in the telogen stage, were incubated with anti-CD34 antibody and prepared (FIG. 2A) for fluorescence-activated cell sorting (FACS). Dct-H2BGFP cells could be separated into distinct CD34(+) and CD34(−)populations using FACS.

Example 4

Separation of Bulge/LPP and SHG GFP-Expressing MPCs of Telogen HFs

Although the percentage yield of cells comprising these populations differed slightly between experiments, in general 0.1-0.3% of the dermal cell suspension contained CD34 (+) and 0.5-1.0% CD34(−)Dct-H2BGFP cells (FIG. 2B), comparable to previous findings with iDct-GFP mice. To further evaluate the specificity of these cell populations, RNA was isolated and relative gene expression for specific marker genes determined (FIG. 2C). These results confirmed that Dct-H2BGFP cells expressed endogenous Dct at significantly higher levels than the basal keratinocyte gene Krt14, with Dct expression marginally higher in CD34(−) Dct-H2BGFP cells compared to CD34(+) counterparts. Furthermore, Cd34 expression was significantly higher in the CD34(+) Dct-H2BGFP cells, with expression of Cdh3, encoding P-cadherin, reciprocally elevated in the CD34(−) Dct-H2BGFP cells corresponding to the P-cadherin-expression SHG population.

Example 5

Figure 3B:
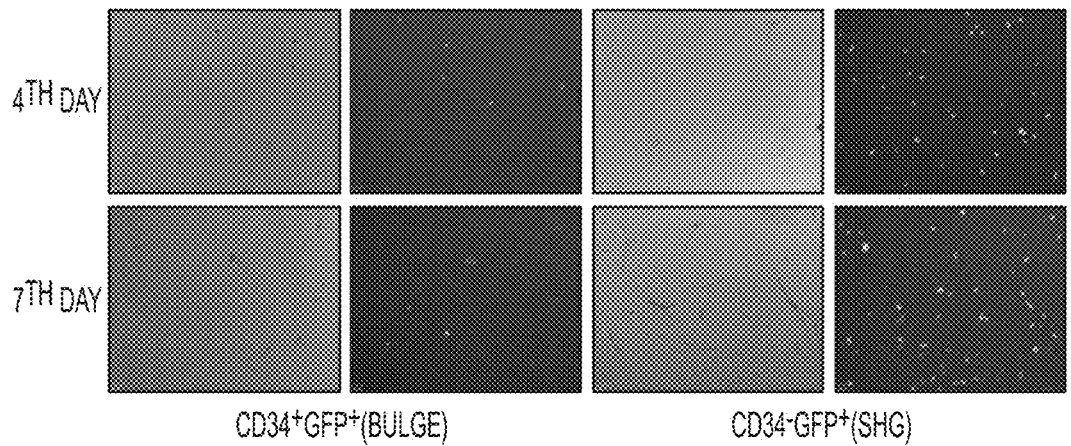
Figure 3C:
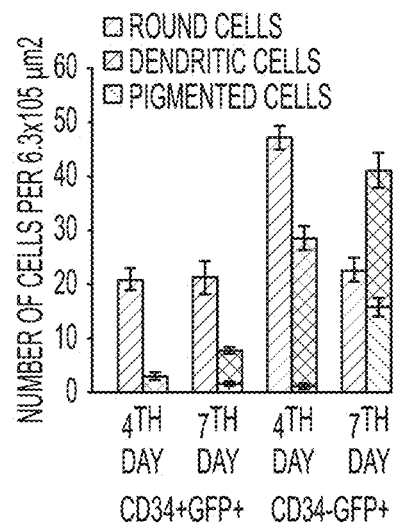

Quantitation of Melanogenic Markers in CD34(+) and CD34(−)MeSCs from Telogen HFs of Dct-H2BGFP$^{ki}$ Mice and Distinct Melanogenic Properties of Bulge/LPP and SHG MPCs of Telogen HFs The ability to separate subsets of HF MeSCs, defined by Dct-H2BGFP expression during telogen, prompted the evaluation of the relative expression of the melanogenic genes Tyr, Tyrp1, and Dct within these subsets. Quantitative RT-PCR results (FIG. 3A) showed that relative expression of all three melanogenic genes measured was significantly higher in the CD34 (−)MeSCs present in the SHG compared to the CD34 (+) cells from the HF bulge/LPP, suggesting that the SHG MeSCs are at a more advanced state of melanocytic differentiation than the cells in the bulge/LPP. To test this notion functionally, cells were sorted, cultured in melanocyte differentiation medium, and observed after 4 and 7 days in culture. Only cultured cells in the CD34(−) Dct-H2BGFP cell culture exhibited visible pigmentation following these in vitro culture periods (FIG. 3B). Quantification of cell pigmentation and morphology (FIG. 3C) confirmed that significant numbers of pigmented cells only developed in the cultures of CD34(−) Dct-H2BGFP cells, with CD34(+) MeSCs principally maintaining a round, rather than dendritic, non-pigmented appearance even after 7 days of in vitro culture in melanocyte differentiation program. These findings provided further evidence that the CD34(+) bulge/LPP MeSC population is functionally distinct from the CD34(−)SHG population.

Example 6

Figure 4A:
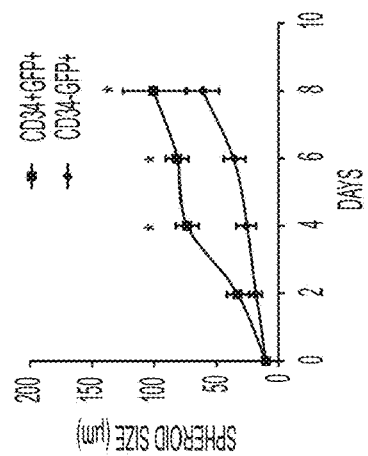
FIG. 4A-4E are photographs and bar graphs illustrating CD34(+) bulge/LPP MeSCs exhibiting distinct neural crest lineage potential.
Figure 4B:
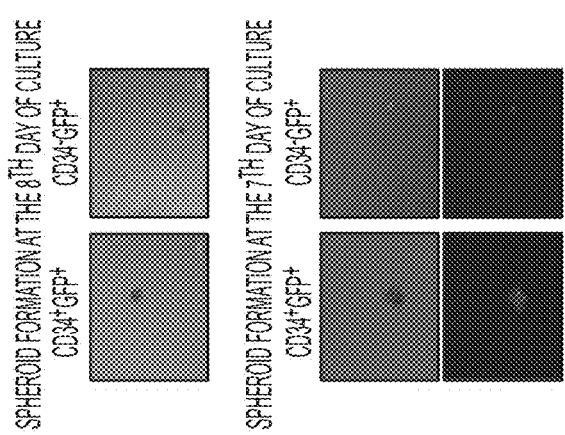
Figure 4C:
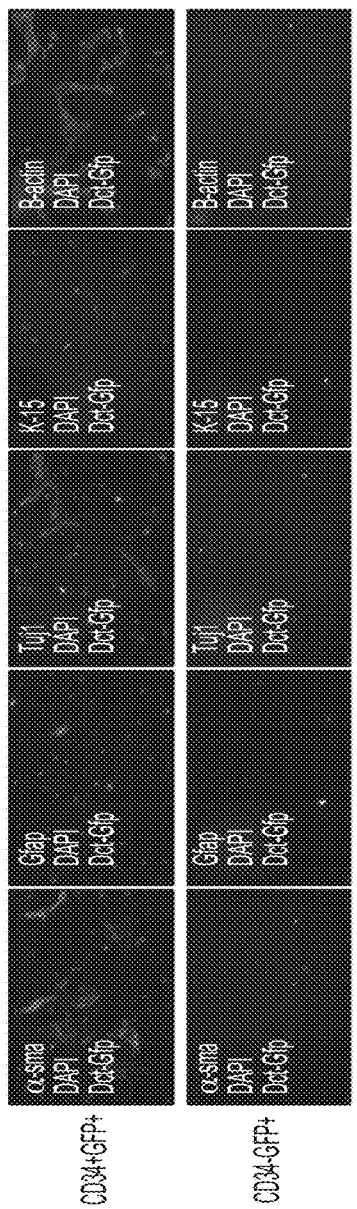
Figure 4D:
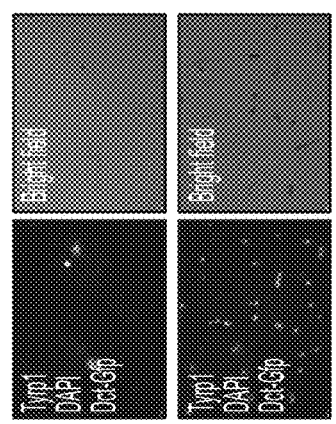

CD34(+) Bulge/LPP MeSCs Exhibit Distinct Neural Crest Lineage Potential in Forming Non-Adherent Spheroids and Exhibiting Multiple Lineage Markers A prior study described skin-derived cells, expressing neural crest cell markers p75 and Sox10, with both capable of growing in culture as spheroids under non-adherent conditions. These cells were reported to exhibit both melanocyte and glial differentiation potential [Wong, 2006]. Based upon this observation, the ability of CD34(+) and CD34(−)cells to grow as spheroids under non-adherent conditions in neural crest stem cell (NCSC) medium was tested. Both populations of cells were capable of growth as spheroids, although spheroids from CD34(+) MeSCs were larger than those from CD34(−) MeSCs (FIG. 4A, FIG. 4B). Cells growing as spheroids were placed in adherent, neural crest cell culture conditions and studied for expression of proteins characteristically expressed by distinct, neural crest-derived cell types, such as Gfap as a marker of glial cells, Tuj1 antigen (β3-tubulin) as a marker of neurons, and α-smooth muscle actin (Sma) as a marker of myofibroblasts [Morrison, 1999], as well as the primitive keratin Krt15. Only adherent cells derived from CD34(+) MeSCs expressed this diversity of neural crest-derived cell markers (FIG. 4C). Adherent cells derived from CD34(+) and CD34 (−)MeSC spheroids both showed expression of the melanocyte marker Tyrp1, although only cells derived from CD34 (−)MeSCs also revealed visible pigmentation (FIG. 4D). Quantification of the expression of markers in individual cells (FIG. 4E) showed that of all the neural crest-derived cell type markers expressed in cells derived from CD34(+)

Figure 4E:
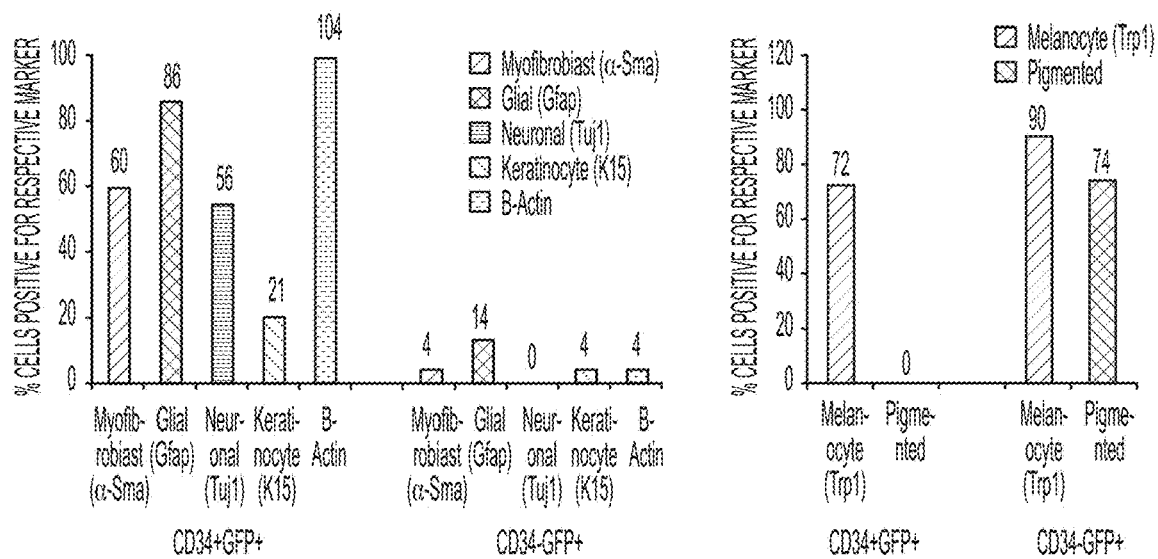

MeSCs, Gfap was the most frequently expressed. Tyrp1 was expressed in the majority of cells cultured in melanocyte differentiation medium derived either from CD34(+) or CD34(−)MeSCs, although the percentage of Tyrp1-expressing cells was higher in adherent cells derived initially from CD34(−)MeSCs (FIG. 4E).

Example 7

Figure 5A:
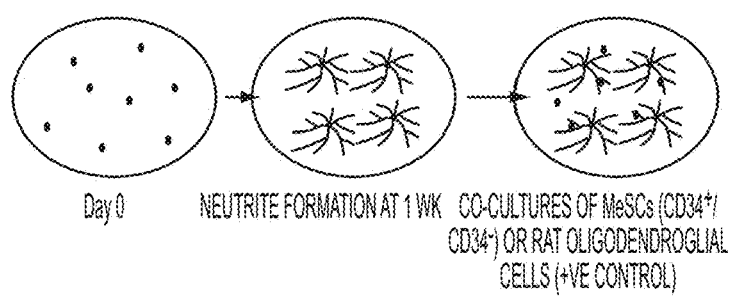
FIG. 5A-5E are photographs illustrating in vitro myelination properties of CD34(+) bulge/LPP MeSCs.

CD34(+) Bulge/LPP MeSCs Expressing Mbp are Able to Myelinate Neurites in an eDRG Co-Culture System Frequent expression of Gfap in cellular derivatives of CD34(+) MeSCs, as well as the glial and melanocyte potential reported from skin-derived neural crest-like stem cells [Wong, 2006], suggested that the CD34(+) MeSC subset might possess the ability to differentiate as glia in culture. To test this notion, systems used previously were adapted to study the ability of oligodendroglial cells (ODCs) to myelinate neurons [Colognato, GLIA 55: 537-545 2007.] to the MeSC system. Dorsal root ganglia (DRG) were isolated from either wild-type or Shiverer (shi/shi) mice. Mice of the shi/shi genotype lack myelin basic protein (Mbp) and develop a "shivering" phenotype, or tremor, eventually dying between 3-4 months of age. CD34(+) and CD34(−)MeSCs, and rat ODCs as positive controls, were co-cultured with neurites extending from wild-type or shi/shi DRGs and studied for their ability to express Mbp in a neuronal distribution (FIG. 5A).

Figure 5B:
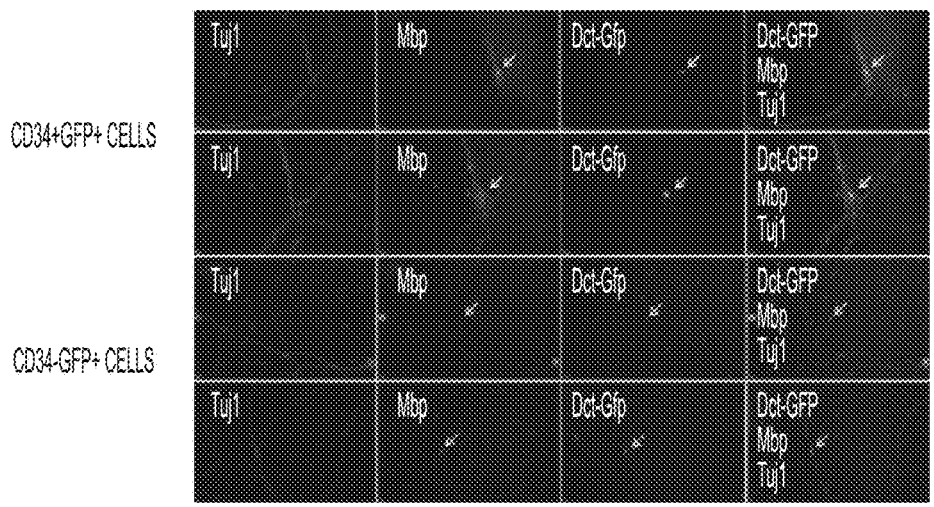
Figure 5C:
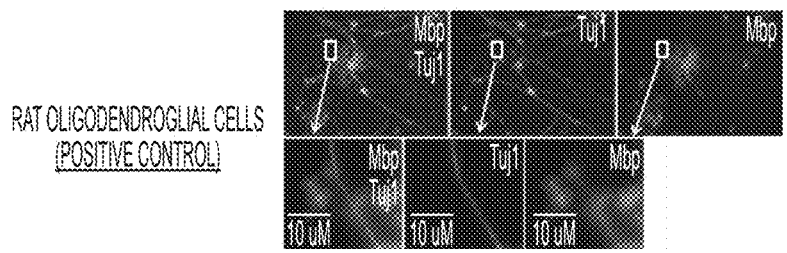
Figure 5D:
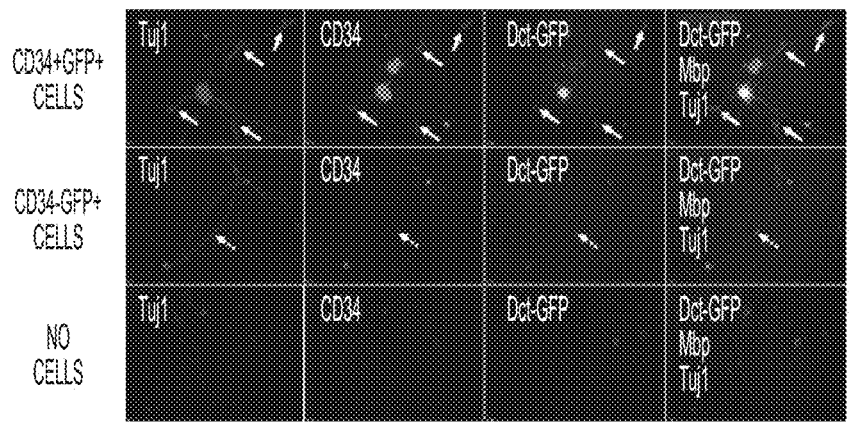
Figure 5E:
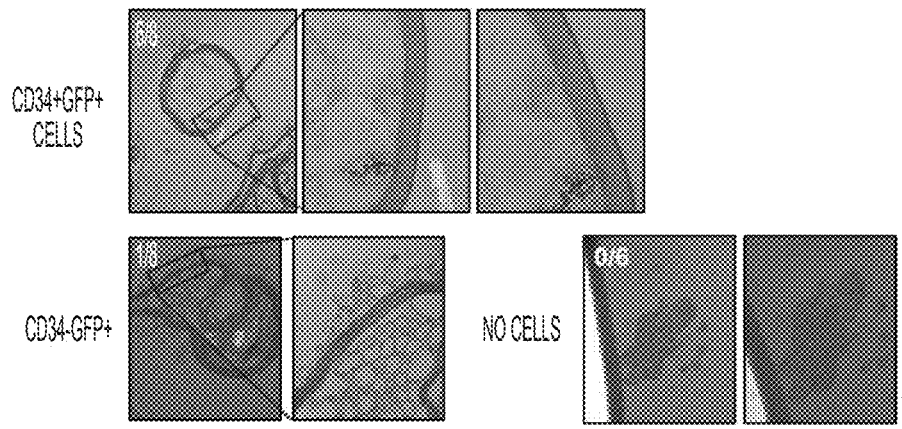

In co-cultures with rat DRGs, CD34(+) MeSCs selectively exhibited Mbp expression in their vicinity in a neuronal pattern (FIG. 5B), similar to the pattern of Mbp expression observed with rat ODGs on shi/shi neurites as a positive control (FIG. 5C). Furthermore, CD34(+) MeSCs also selectively exhibited the ability to express Mbp along shi/shi neurites (FIG. 5D), compared with CD34(−)MeSCs or no added cells. This result suggested that CD34(+) bulge/LPP MeSCs selectively possess the ability to generate a de novo myelin sheath. To determine the ability of CD34(+) MeSCs to generate compact myelin indicative of functional myelination, co-cultures of CD34(+) and CD34(−) MeSCs with shi/shi DRGs were again initiated, with resulting cultures examined using electron microscopy (EM) for evidence of compact myelin surrounding neurites in the vicinity of MeSC cell bodies. EM analysis of co-cultures of CD34(+) MeSCs revealed evidence of compact myelin in ⅝ cultures. In contrast, a loose myelin sheath was detected in only ⅛ CD34(−)MeSC co-cultures, and no myelin sheath was observed surrounding shi/shi neurites when no MeSCs were added.

Example 8

In Vivo Demyelination Animal Model and Use of CD34(+) MeSCs for Remyelination of Neuronal Axons Several animal models of demyelination exist, including experimental autoimmune encephalomyelitis, experimental autoimmune neuritis, cuprizone model for toxic demyelination, and Theiler's viral induced encephalitis. Homozygous shiverer (Shi) mice are widely used as a model of demyelinating disorders. Shi mice have a spontaneous deletion of multiple exons in the gene encoding myelin basic protein (MBP), which results in pronounced ataxia by 2 to 3 weeks of age and the onset of fatal seizures by ~8 to 14 weeks (3-6). One variant of this model is the immunodeficient Shi×RAG2−/− mouse, which displays a milder CNS phenotype and a longer life span of ~18 to 21 weeks. Delivery of freshly isolated human oligodendrocyte progenitor cells from the brain tissue of fetuses at 9 to 22 weeks of gestation into multiple CNS sites in asymptomatic newborn Shi×RAG2−/− mice resulted in diffuse CNS myelination and markedly prolonged survival in some of the animals.

We will provide in vivo data showing that indirect and direct administration in vivo of CD34(+) multipotent neural crest progenitor cells to myelin basic protein (MBP)-deficient mice in a demyelination animal model will attenuate clinical symptoms. Evidence of indirect administration in vivo will include dorsal root ganglion treated ex vivo with CD34(+) MeSCs and re-implanted into the area of demyelination will drastically reduce symptoms. Mice will be given CD34(+) multipotent neural crest progenitor cells in an amount ranging from 100 μg/100 μl/mouse via intraperitoneal injection, intrathecal injection, or intralesional injection at day 0, day 4, day 7, and day 10. Clinical symptoms will be assessed according to a clinical score system. These results show that CD34(+)multipotent neural crest progenitor cells administered to mice having a demyelinating disease will have therapeutic utility and dramatically reduce the symptoms of the disease. These results will provide in vivo evidence that demyelinating diseases can be treated by direct administration of therapeutically effective amounts of CD34(+) multipotent neural crest progenitor cells to an animal in vivo.

REFERENCES

All references cited herein are hereby incorporated by reference in their entirety.

Estrach S, Ambler C A, Lo Celso C, Hozumi K, Watt F M. Jagged 1 is a beta-catenin target gene required for ectopic hair follicle formation in adult epidermis. Development. 2006 November; 133(22):4427-38. Epub 2006 Oct. 11.

Braun K M, Niemann C, Jensen U B, Sundberg J P, Silva-Vargas V, Watt F M. Manipulation of stem cell proliferation and lineage commitment: visualization of label-retaining cells in whole mounts of mouse epidermis. Development. 2003 November; 130(21):5241-55. Epub 2003 Sep. 3.

Bixby S, Kruger G M, Mosher J T, Joseph N M, Morrison S J. Cell-intrinsic differences between stem cells from different regions of the peripheral nervous system regulate the generation of neural diversity. Neuron. 2002 Aug. 15; 35(4):643-56.

Pfaltzgraff E R, Mundell N A, Labosky P A. Isolation and culture of neural crest cells from embryonic murine neural tube. J Vis Exp. 2012 Jun. 2; (64):e4134. doi: 10.3791/4134.

O'Meara R W, Ryan S D, Colognato H, Kothary R. Derivation of enriched oligodendrocyte cultures and oligodendrocyte/neuron myelinating co-cultures from post-natal murine tissues. J Vis Exp. 2011 Aug. 21; (54). pii: 3324. doi: 10.3791/3324.

What is claimed is:

1. A method of producing a functional myelin sheath on one or more neurites of neurons that lack a functional myelin sheath, comprising contacting the neurons with isolated myelin-depositing cells which:
   (a) are CD34(+) melanocyte stem cells from the bulge region, the lower permanent portion, or both, of the hair follicle of a mammal that have been exposed to neural crest differentiation medium also containing 10 μM ascorbic acid;
   (b) have no visible pigmentation;
   (c) express glial fibrillary acid protein, and Tuj1 (β3-tubulin); and
   (d) express myelin basic protein and produce a functional multilayered myelin sheath surrounding the neurites of unmyelinated neurons when contacted with the unmyelinated neurites,
   wherein contacting is achieved by co-culturing the CD34 (+) multipotent neural crest progenitor cells and neurons that lack a functional myelin sheath together in poly-D-lysine and laminin-coated vessels in neural crest differentiation medium including 10 μM ascorbic acid.

2. A method of producing a functional myelin sheath on one or more neurites of neurons that lack a functional myelin sheath, comprising contacting the neurons with isolated myelin-depositing cells which:
   (a) are CD34(+) melanocyte stem cells from the bulge region, the lower permanent portion, or both, of the hair follicle of a mammal that have been exposed to neural crest differentiation medium also containing 10 μM ascorbic acid;
   (b) have no visible pigmentation;
   (c) express glial fibrillary acid protein, and Tuj1 (β3-tubulin); and
   (d) express myelin basic protein and produce a functional multilayered myelin sheath surrounding the neurites of unmyelinated neurons when contacted with the unmyelinated neurites,
   wherein contacting is achieved by direct injection, intrathecal injection, intravenous injection, or stereotaxic injection of the CD34(+) multipotent neural crest progenitor cells into a subject having neurons that lack a functional myelin sheath.

3. The method of claim 2 wherein the neurons that lack a functional myelin sheath are in the-peripheral nervous system of the subject.

4. The method of claim 2 wherein the neurons that lack a functional myelin sheath are in the-central nervous system of the subject.

5. The method of claim 2 wherein the subject suffers from demyelination.

6. The method of claim 5 wherein the demyelination is caused by trauma, a toxin, a bacterial infection, a viral infection, a parasitic infection, an autoimmune disease or a demyelinating disease.

7. The method of claim 6 wherein the demyelinating disease is selected from the group consisting of experimental allergic encephalomyelitis, acute disseminated encephalomyelopathy, acute hemorrhagic encephalomyelopathy, experimental allergic neuritis, amoebic meningoencephalitis, Guillain-Barre syndrome, multiple sclerosis, stroke, traumatic brain injury, traumatic peripheral nerve injury, Devic's disease (otherwise known as neuromyelitis optica (NMO)), NMO spectrum disorder, progressive multifocal leukoencephalopathy, central pontine myelinolysis, Tabes *dorsalis*, optic neuritis, transverse myelitis, progressive inflammatory neuropathy, myelopathy, chronic inflammatory demyelinating polyneuropathy, Charcot-Marie-Tooth disease, and visna.

* * * * *

SEQUENCE LISTING

<160> NUMBER OF SEQ ID NOS: 20

<210> SEQ ID NO 1
<211> LENGTH: 18
<212> TYPE: DNA
<213> ORGANISM: Artificial Sequence
<220> FEATURE:
<223> OTHER INFORMATION: Synthetic primer: Mouse Dct Forward

<400> SEQUENCE: 1
ttcgcaaagg ctatgcgc                                                  18

<210> SEQ ID NO 2
<211> LENGTH: 22
<212> TYPE: DNA
<213> ORGANISM: Artificial Sequence
<220> FEATURE:
<223> OTHER INFORMATION: Synthetic primer: Mouse Dct Reverse

<400> SEQUENCE: 2
gttactaccc aggtcaggcc ag                                             22

<210> SEQ ID NO 3
<211> LENGTH: 20
<212> TYPE: DNA
<213> ORGANISM: Artificial Sequence
<220> FEATURE:
<223> OTHER INFORMATION: Synthetic primer: Mouse Cytokeratin 14 Forward

<400> SEQUENCE: 3
atcgaggacc tgaagagcaa                                                20

<210> SEQ ID NO 4
<211> LENGTH: 20
<212> TYPE: DNA
<213> ORGANISM: Artificial Sequence
<220> FEATURE:
<223> OTHER INFORMATION: Synthetic primer: Mouse Cytokeratin 14 Reverse

<400> SEQUENCE: 4
ggctctcaat ctgcatctcc                                                20

<210> SEQ ID NO 5
<211> LENGTH: 17
<212> TYPE: DNA
<213> ORGANISM: Artificial Sequence
<220> FEATURE:
<223> OTHER INFORMATION: Synthetic primer: Tyr Reverse

<400> SEQUENCE: 5
tgccttcgca gccattg                                                   17

<210> SEQ ID NO 6
<211> LENGTH: 24
<212> TYPE: DNA
<213> ORGANISM: Artificial Sequence
<220> FEATURE:
<223> OTHER INFORMATION: Synthetic primer: Tyrp1 Forward

<400> SEQUENCE: 6
gtgttcccta gctcagttct ctgg                                           24

<210> SEQ ID NO 7
<211> LENGTH: 18
<212> TYPE: DNA
<213> ORGANISM: Artificial Sequence

```
<220> FEATURE:
<223> OTHER INFORMATION: Synthetic primer: Tyrp1 Reverse

<400> SEQUENCE: 7
tcctctgact gatacctt                                                      18

<210> SEQ ID NO 8
<211> LENGTH: 22
<212> TYPE: DNA
<213> ORGANISM: Artificial Sequence
<220> FEATURE:
<223> OTHER INFORMATION: Synthetic primer: Gapdh Reverse

<400> SEQUENCE: 8
tgtagcccaa gatgcccttc ag                                                 22

<210> SEQ ID NO 9
<211> LENGTH: 24
<212> TYPE: DNA
<213> ORGANISM: Artificial Sequence
<220> FEATURE:
<223> OTHER INFORMATION: Synthetic primer: Pmel17 Forward

<400> SEQUENCE: 9
tccaggaatc aggactggct tggt                                               24

<210> SEQ ID NO 10
<211> LENGTH: 20
<212> TYPE: DNA
<213> ORGANISM: Artificial Sequence
<220> FEATURE:
<223> OTHER INFORMATION: Synthetic primer: Pmel17 Reverse

<400> SEQUENCE: 10
gtgaaggttg aactggcgtg                                                    20

<210> SEQ ID NO 11
<211> LENGTH: 20
<212> TYPE: DNA
<213> ORGANISM: Artificial Sequence
<220> FEATURE:
<223> OTHER INFORMATION: Synthetic primer: P-Cad FWD

<400> SEQUENCE: 11
acagcatcac agggcctggc                                                    20

<210> SEQ ID NO 12
<211> LENGTH: 20
<212> TYPE: DNA
<213> ORGANISM: Artificial Sequence
<220> FEATURE:
<223> OTHER INFORMATION: Synthetic primer: P-Cad REV

<400> SEQUENCE: 12
tggctccttc ggctcttggc                                                    20

<210> SEQ ID NO 13
<211> LENGTH: 20
<212> TYPE: DNA
<213> ORGANISM: Artificial Sequence
<220> FEATURE:
<223> OTHER INFORMATION: Synthetic primer: Mbpshi Fwd

<400> SEQUENCE: 13
accgtcctga gaccattgtc                                                    20
```

```
<210> SEQ ID NO 14
<211> LENGTH: 24
<212> TYPE: DNA
<213> ORGANISM: Artificial Sequence
<220> FEATURE:
<223> OTHER INFORMATION: Synthetic primer: Mbpshi Rev

<400> SEQUENCE: 14
gtgcttatct agtgtatgcc tgtg                                          24

<210> SEQ ID NO 15
<211> LENGTH: 20
<212> TYPE: DNA
<213> ORGANISM: Artificial Sequence
<220> FEATURE:
<223> OTHER INFORMATION: Synthetic primer: Control Fwd

<400> SEQUENCE: 15
caaatgttgc ttgtctggtg                                               20

<210> SEQ ID NO 16
<211> LENGTH: 20
<212> TYPE: DNA
<213> ORGANISM: Artificial Sequence
<220> FEATURE:
<223> OTHER INFORMATION: Synthetic primer: Control Rev

<400> SEQUENCE: 16
gtcagtcgag tgcacagttt                                               20

<210> SEQ ID NO 17
<211> LENGTH: 21
<212> TYPE: DNA
<213> ORGANISM: Artificial Sequence
<220> FEATURE:
<223> OTHER INFORMATION: Synthetic primer: WTshi Fwd

<400> SEQUENCE: 17
ggccggaccc aagatgaaaa c                                             21

<210> SEQ ID NO 18
<211> LENGTH: 21
<212> TYPE: DNA
<213> ORGANISM: Artificial Sequence
<220> FEATURE:
<223> OTHER INFORMATION: Synthetic primer: WTshi Rev

<400> SEQUENCE: 18
tgttggccta aagcacccta c                                             21

<210> SEQ ID NO 19
<211> LENGTH: 17
<212> TYPE: DNA
<213> ORGANISM: Artificial Sequence
<220> FEATURE:
<223> OTHER INFORMATION: Synthetic primer: Tyr Forward

<400> SEQUENCE: 19
cggccaacga tcccatt                                                  17
```

```
<210> SEQ ID NO 20
<211> LENGTH: 25
<212> TYPE: DNA
<213> ORGANISM: Artificial Sequence
<220> FEATURE:
<223> OTHER INFORMATION: Synthetic primer: Gapdh Forward

<400> SEQUENCE: 20
tgcagtggca aagtggagat tgttg                                         25
```